(12) United States Patent
Cooper et al.

(10) Patent No.: US 7,250,505 B1
(45) Date of Patent: Jul. 31, 2007

(54) ISOLATION AND EXPRESSION OF A DISABLED PROTEIN GENE MDAB1 AND METHODS

(75) Inventors: Jonathan A. Cooper, Seattle, WA (US); Brian W. Howell, Rockville, MD (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 09/486,293

(22) PCT Filed: Aug. 21, 1998

(86) PCT No.: PCT/US98/17384

§ 371 (c)(1),
(2), (4) Date: Aug. 22, 2000

(87) PCT Pub. No.: WO99/09153

PCT Pub. Date: Feb. 25, 1999

Related U.S. Application Data

(60) Provisional application No. 60/056,473, filed on Aug. 21, 1997.

(51) Int. Cl.
*C12N 15/09* (2006.01)
*C07K 14/47* (2006.01)
*A61K 39/395* (2006.01)

(52) U.S. Cl. .................. 536/23.5; 435/320.1; 435/325; 435/410; 435/252.3; 435/254.2; 435/23.1

(58) Field of Classification Search ............... 536/23.5, 536/24.3, 23.1; 435/320.1, 325, 410, 252.3, 435/254.2
See application file for complete search history.

(56) References Cited

U.S. PATENT DOCUMENTS 4,816,397 A 3/1989 Boss et al.

FOREIGN PATENT DOCUMENTS

WO WO 97/10252 3/1997

OTHER PUBLICATIONS

Ware LM et.al., "Aberrent Splicingof a mouse disabled Homolog, mdab1, in the scrambler mouse". Neuron vol. 19., p. 239-249, (1997).*
Gertler et. et. al., reference BH of applicants IDS "Dosage sensitive modifiers of Dosophila abl tyrosine kinase function: prospero a regulator of axonal outgrowth and disabled a novel tyrosine kinase substrate," Gene development, 7, 441-453 (1993).*
Brian W. H. et. al., reference DV of applicants IDS, Mouse disabled (mdab1): a Src binding protein implicated in neuronal development, EMBO J. 16: 121-132. (1997).*
Howell et. al, Genbank accession Y08379, Jan. 1997.*
Howell et. al. (Mouse disabled (mDab1): a Src binding protein implicated in neuronal development. EMBO journal vol. 16, No. 1, pp. 121-132, 1997.*
Caviness et al., "Retrohippocampal, Hippocampal and Related-Structures of the Forebrain in the Reeler Mutant Mouse," *J. Comp. Neur.* 147: 235-254 (1973).
Goffinet, "An Early Developmental Defect in the Cerebral Cortex of the Reeler Mouse," *Anat. Embryol.* 157: 205-216 (1979).
Stanfield and Cowan, "The Morphology of the Hippocampus and Dentate Gyrus in Normal and Reeler Mice," *J. Comp. Neur.* 185: 393-422 (1979).
Caviness, "Neocortical Histogenesis in Normal and Reeler Mice: A Developmental Study Based Upon [$^3$H] Thymidine Autoradiography," *Brain Res.* 4: 293-302 (1982).
Goffinet, "Events Governing Organization of Postmigratory Neurons: Studies on Brain Development in Normal and Reeler Mice," *Brain Res.* 7: 261-296 (1984).
Goffinet et al., "Architectonic and Hodological Organization of the Cerebellum in Reeler Mutant Mice," *Brain Res.* 16: 263-276 (1984).
Simon et al., "The Nucleotide Sequence and the Tissue-Specific Expression of Drosophila c-src," *Cell* 42: 831-840 (1985).
Cooper et al., "Tyr$^{527}$ is Phosphorylated in pp60$^{C-src}$: Implications for Regulation," *Science* 231: 1431-1434 (1986).
Henkemeyer et al., "The *Drosophila* Abelson Proto-Oncogene Homolog: Identification of Mutant Alleles That Have Pleiotropic Effects Late in Development," *Cell* 51: 821-828 (1987).
Cooper and MacAuley, "Potential Positive and Negative Autoregulation of p60$^{c-src}$ by Intermolecular and Autophosphorylation," *Proc. Natl. Acad. Sci. USA* 85: 4232-4236 (1988).
MacAuley and Cooper, "The Carboxy-Terminal Sequence of p56$^{lck}$ Can Regulate p60$^{c-src}$," *Mol. Cell. Biol.* 8: 3560-3564 (1988).
Elkins et al., "Genetic Analysis of a *Drosophila* Neural Cell Adhesion Molecule: Interaction of Fasciclin I and Abelson Tyrosine Kinase Mutations," *Cell* 60: 565-575 (1990).
Druker et al., "Oncogenes, Growth Factors, and Signal Transduction," *New Eng. J. Med.* 321: 1383-1391 (1989).
Gertler et al., "*Drosophila abl* Tyrosine Kinase in Embryonic CNS Axons: A Role in Axogenesis is Revealed Through Dosage-Sensitive Interactions with *disabled*," *Cell* 58: 103-113 (1989).
Elkins et al., "Genetic Analysis of a *Drosophila* Neural Cell Adhesion Molecule: Interaction of Fasciclin I and Abelson Tyrosine Kinase Mutations," *Cell* 60: 565-575 (1990).
Gertler et al., "Genetic Suppression of Mutations in the *Drosophila abl* Proto-Oncogene Homolog," *Science* 248: 857-860 (1990).
Henkemeyer et al., "A Novel Tyrosine Kinase-Independent Function of *Drosophila abl* Correlates with Proper Subcellular Localization," *Cell* 63: 949-960 (1990).

(Continued)

*Primary Examiner*—Kathleen Kerr Bragdon
*Assistant Examiner*—Kagnew Gebreyesus
(74) *Attorney, Agent, or Firm*—Townsend and Townsend and Crew LLP

(57) ABSTRACT

A mammalian homology of *Drosophila* Disabled protein has been identified and cloned. In particular, the murine homolog designated mDab1 has been cloned and expressed. mDab1, when tyrosine phosphorylated, binds to the SH2 domain of Src, Abl and Fyn. Antibodies specific for mDab1 are provided as are methods for the screening of agents for their ability to modulate mDab1 activity. Methods for diagnosing Disabled protein associated disease are also provided.

12 Claims, No Drawings

OTHER PUBLICATIONS

Maness et al., "Localization of the Normal Cellular *Src* Protein to the Growth Cone of Differentiating Neurons in Brain and Retina," *Adv. Exp. Med. Biol.* 265: 117-125 (1990).

Bixby and Harris, "Molecular Mechanisms of Axon Growth and Guidance," *Annu. Rev. Cell Biol.* 7: 117-159 (1991).

Kremer et al., "Signal Transduction by Nerve Growth Factor and Fibroblast Growth Factor in PC12 Cells Requires a Sequence of Src and Ras Actions," *J. Cell Biol.* 115: 809-819 (1991).

Lannoo et al., "Zebrin II Immunoreactivity in the Rat and in Weakly Electric Teleost *Eigenmannia* (Gymnotiformes) Reveals Three Modes of Purkinje Cell Development," *J. Comp. Neurol.* 310: 215-233 (1991).

Schwartzberg et al., "Mice Homozygous for the $abl^{m1}$ Mutation Show Poor Viability and Depletion of Selected B and T Cell Populations," *Cell* 65: 1165-1175 (1991).

Tybulewicz, et al., "Neonatal Lethality and Lymphopenia in Mice with a Homozygous Disruption of the c-*abl* Proto-Oncogence," *Cell*: 1153-1163 (1991).

Vaessin et al., "*prospero* is Expressed in Neuronal Precursors and Encodes a Nuclear Protein That is Involved in the Control of Axonal Outgrowth in *Drosophila*," *Cell* 67:941-953 (1991).

Bennett and Hoffman, "Increased Levels of the *Drosophila* Abelson Tyrosine Kinase in Nerves and Muscles: Subcellular Localization and Mutant Phenotypes Imply a Role in Cell-cell Interactions," *Development* 116: 953-966 (1992).

Maness, "Nonreceptor Protein Tyrosine Kinases Associated with Neuronal Development," *Dev. Neurosci* 14: 257-270 (1992).

Mayer et al., "Point Mutations in the *abl* SH2 Domain Coordinately Impair Phosphotyrosine Binding In Vitro and Transforming Activity in Vivo," *Mol. Cell Biol.* 12: 609-618 (1992).

McConnell, "The Control of Neuronal Identity in the Developing of Cerebral Cortex," *Curr. Opin. Neurobiol.* 2:23-27 (1992).

Seidel-Dugan et al., "Effects of SH2 and SH3 Deletions on the Functional Activities of Wild-Type and Transforming Variants of c-Src," *Mol. Cell. Biol.* 12: 1835-1845 (1992).

Stein et al., "pp59$^{fyn}$ Mutant Mice Display Differential Signaling in Thymocytes and Peripheral T Cells," *Cell* 70: 741-750 (1992).

Waksman et al., "Crystal Structure of the Phosphotyrosine Recognition Domain SH2 of v-*src* Complexed with Tyrosine-phosphorylated Peptides," *Nature* 358: 646-653 (1992).

Gertler et al., "Dosage-sensitive Modifiers of *Drosophila abl* Tyrosine Kinase Function: *prospero*, a Regulator of Axonal Outgrowth,and *disabled*, a Novel Tyrosine Kinase Substrate," *Genes Dev.* 7: 441-453 (1993).

Hatten, "The Role of Migration in Central Nervous System Neuronal Development," *Curr. Opin. Neurobiol.* 3: 38-44 (1993).

Kussick et al., "Ras 1-dependent Signaling by Ectopically-expressed *Drosophila src* Gene Product in the Embryo and Developing Eye," *Oncogene*, 8: 2791-2803 (1993).

Mori, et al., "Identification of Two Juxtamembrane Autophosphorylation Sites in the PDGF β-receptor; Involvement in the Interaction with Src Family Tyrosine Kinases," *EMBO J.*, 6: 2257-2264 (1993).

Okada et al., "Deletion of the SH3 Domain of Src Interferes with Regulation by the Phosphorylated Carboxyl-terminal Tyrosine," *J. Biol. Chem.* 268: 18070-18075 (1993).

Songyang et al., "SH2 Domains Recognize Specific Phosphopeptide Sequences," *Cell* 72: 767-778 (1993).

Vojtek et al., "Mammalian Ras Interacts Directly with the Serine/Threonine Kinase Raf," *Cell* 74: 205-214 (1993).

Vojtek and Cooper, "Identification and Characterization of a cDNA Encoding Mouse CAP: a Homolog of the Yeast Adenylyl Cyclase Associated Protein," *J. Cell Sci.* 105: 777-785 (1993).

Wu and Goldberg, "Regulated Tyrosine Phosphorylation at the Tips of Growth Cone Filopodia," *J. Cell Biol.* 123: 653-664 (1993).

Beggs et al., "NCAM-dependent Neurite Outgrowth Is Inhibited in Neurons from *Fyn*-minus Mice," *J. Cell. Biol.* 127: 825-833 (1994).

Cobb et al., "Stable Association of pp60$^{src}$ and pp59$^{fyn}$ with the Focal Adhesion-Associated Protein Tyrosine Kinase, pp125$^{FAK}$," *Mol. Cell. Biol.* 14: 147-155 (1994).

Feng et al., "Two Binding Orientations for Peptides to the Src SH3 Domain: Development of a General Model for SH3-Ligand Interactions," *Science* 266: 1241-1247 (1994).

Fumagalli et al., "A Target for Src in Mitosis," *Nature* 368: 871-874 (1994).

Howell and Cooper, "Csk Suppression of Src Involves Movement of Csk to Sites of Src Activity," *Mol. Cell. Biol.* 14: 5402-5411 (1994).

Ignelzi et al., "Impaired Neurite Outgrowth of *src*-Minus Cerebellar Neurons on the Cell Adhesion Molecule L 1," *Neuron* 12: 873-884 (1994).

Kavanaugh and Williams, "An Alternative to SH2 Domains for Binding Tyrosine Phosphorylated Proteins," *Science* 266: 1862-1865 (1994).

Mok et al., "Molecular Cloning of Differentially Expressed Genes in Human Epithelial Ovarian Cancer," *Gyn Oncol.* 52: 247-252 (1994).

Sabe et al., "Analysis of the Binding of the Src Homology 2 Domain of Csk to Tyrosine-phosphorylated Proteins in the Suppression and Mitotic Activation of c-Src," *Proc. Natl. Acad. Sci. USA* 91: 3984-3988 (1994).

Schaller et al., "Autophosphorylation of the Focal Adhesion Kinase, pp125$^{FAK}$, Directs SH2-Dependent Binding of pp60$^{src}$," *Mol. Cell. Biol.* 14: 1680-1688 (1994).

Snider, "Functions of the Neurotrophins during Nervous System Development: What the Knockouts Are Teaching Us," *Cell* 77: 627-638 (1994).

Taylor and Shalloway, "An RNA-binding Protein Associated with Src Through its SH2 and SH3 Domains in Mitosis,"*Nature* 368: 867-871 (1994).

Umemori et al., "Initial Events of Myelination Involve Fyn Tyrosine Kinase Signalling," *Nature* 367: 572-576 (1994).

Wilson et al., "2.2 Mb of Continguous Nucleotide Sequence From Chromosome III of *C. elegans*," *Nature* 368: 32-38 (1994).

Yu et al., "Structural Basis for the Binding of Proline-Rich Peptides to SH3 Domains," *Cell* 76: 933-945 (1994).

Alonso et al., "Sequence Requirements for Binding of Src Family Tyrosine Kinases to Activated Growth Factor Receptors," *J. Biol. Chem.* 270: 9840-9848 (1995).

Bazter et al, "The Phosphotyrosine Interaction Domain of Shc Binds an LXNPXY Motif on the Epidermal Growth Factor Receptor," *Mol. Cell. Biol.* 15: 4403-4409 (1995).

Bork and Margolis, A Phosphotyrosine Interaction Domain, *Cell* 80: 694-694 (1995).

Callahan et al., "Control of Neuronal Pathway Selection by a *Drosophila* Receptor Protein-tyrosine Kinase Family Member," *Nature* 376: 171-174 (1995).

D'Arcangelo et al., "A Protein Related to Extracellular Matrix Proteins Deleted in the Mouse Mutant *reeler,*" *Nature* 374: 719-723 (1995).

Duyster et al., "Src Homology 2 Domains as a Specificity Determinant in the c-Abl-mediated Tyrosine Phosphorylation of the RNA Polymerae II Carboxyl-terminal Repeated Domain," *Proc. Natl. Acad. Sci. USA* 92: 1555-1559 (1995).

Goldberg and Wu, "Inhibition of Formation of Filopodia after Axotomy by Inhibitors of Protein Tyrosine Kinases," *J. Neurobiol.* 27: 553-560 (1995).

Hill et al., "Genetic Interactions Between the *Drosophila* Abelson (Abl) Tyrosine Kinase and Failed Axon Connections (Fax), a Novel Protein in Axon Bundles," *Genetics* 141: 595-606 (1995).

Hirotsune et al., "The Reeler Gene Encodes a Protein with an EGF-like Motif Expressed by Pioneer Neurons," *Nat. Genet.* 10: 77-83 (1995).

Hoffarth et al., "The Mouse Mutation *Reeler* Causes Increased Adhesion within a Subpopulation of Early Postmitotic Cortical Neurons," *J. Neurosci.* 15: 4838-4850 (1995).

Hollenberg et al., "Identification of a New Family of Tissue-Specific Basis Helix-Loop-Helix Proteins with a Two-Hybrid System," *Mol. Cell. Biol.* 15: 3813-3822 (1995).

Kavanaugh et al., "PTB Domain Binding to Signaling Proteins Through a Sequence Motif Containing Phosphotyrosine," *Science* 268: 1177-1179 (1995).

Lai et al., "A *Drosophila shc* Gene Product is Implicated in Signaling by the DER Receptor Tyrosine Kinase," *Mol. Cell. Biol.* 15: 4810-4818 (1995).

Mayer and Eck, "Minding your p's and q's: SH3 Domains Mediate Many Important Protein-protein Interactions. The Molecular Basis of the Binding of These Domains to Their Ligands has been Revealed, Making it Possible to Identify SH3-binding Sites in New Proteins," *Curr. Biol.* 5: 364-367 (1995).

Mc Connell, "Constructing the Cerebral Cortex: Neurogenesis and Fate Determination," *Neuron* 15: 761-768 (1995).

Ogawa et al., "The *reeler* Gene-Associated Antigen on Cajal-Retzius Neurons is a Crucial Molecule for Laminar Organization of Cortical Neurons,"*Neuron* 14: 899-912 (1995).

Smeyne et al., "Local Control of Granule Cell Generation by Cerebellar Purkinje Cells," *Mol. Cell. Biol.* 6: 230-251 (1995).

Songyang et al., "Catalytic Specificity of Protein-tyrosine Kinases is Critical for Selective Signaling," *Nature* 373: 536-539 (1995).

Songyang et al., "The Phosphotyrosine Interaction Domain of SHC Recognizes Tyrosine-phosphorylated NPXY Motif," *J. Biol. Chem.* 270: 14863-14866 (1995).

Tessier-Lavigne, "Eph Receptor Tyrosine Kinases, Axon Repulsion, and the Development of Topographic Maps," *Cell* 82: 345-348 (1995).

Vaillancourt et al., "Mitogen-Activated Protein Kinase Activation is Insufficient for Growth Factor Receptor-Mediated PC 12 Cell Differentiation," *Mol. Cell. Biol.* 15: 3644-3653 (1995).

van der Geer et al., "A Conserved Amino-terminal Shc Domain Binds to Phosphotyrosine Motifs in Activated Receptors and Phosphopeptides," *Curr. Biol.* 5: 404-412 (1995).

Vojtek and Hollenberg, "Ras-Raf. Interaction: Two-Hybrid Analysis," *Meth. Enzymol.* 255: 331-342 (1995).

Xu et al., "Cloning of a Novel Phosphoprotein Regulated by Colony-stimulating Factor 1 Shares a Domain with the *Drosophila disabled* Gene Product," *J. Biol. Chem.* 270: 14184-14191 (1995).

Zheng et al., "β-Amyloid Precursor Protein-Deficient Mice Show Reactive Gliosis and Decreased Locomotor Activity," *Cell* 81: 525-531 (1995).

Zhou et al., "Structure and Ligand Recognition of the Phosphotyrosine Binding Domain of Shc," *Nature* 378: 584-592 (1995).

Albertsen et al., "Sequence, Genomic Structure, and Chromosomal Assignment of Human DOC-2," *Genomics* 33: 207-213 (1996).

Brown and Cooper, "Regulation, Substrates and Functions of src," *Biochim. Biophys. Acta* 1287: 121-149 (1996).

Desai et al., "Receptor Tyrosine Phosphatases Are Required for Motor Axon Guidance in the *Drosophila* Embryo," *Cell* 84: 599-609 (1996).

Eck et al., "Structure of the IRS-1 PTB Domain Bound to the Juxtamembrane Region of the Insulin Receptor," *Cell* 85: 695-705 (1996).

Keegan and Cooper, "Use of the Two Hybrid System to Detect the Association of the Protein-tyrosine-phosphatase, SHPTP2, with Another SH2-containing Protein, Grb7," *Oncogene* 12: 1537-1544 (1996).

Krueger et al., "The Transmembrane Tyrosine Phosphatase DLAR Controls Motor Axon Guidance in *Drosophila,"* *Cell* 84: 611-622 (1996).

Lioubin et al., "p 150$^{Ship}$, a Signal Transduction Molecule with Inositol Polyphosphate-5-phosphatase Activity," *Genes Devel.* 10: 1084-1095 (1996).

Margolis, "The PI/PTB Domain: A New Protein Interaction Domain Involved in Growth Factor Receptor Signaling," *J. Lab. Clin. Med.* 128:235-241 (1996).

Miyata et al., "Distribution of a Reeler Gene-Related Antigen in the Developing Cerebellum: An Immunohistochemical Study With an Allogeneic Antibody CR-50 on Normal and Reeler Mice," *J. Comp. Neurol.* 372: 215-228 (1996).

O'Bryan et al., "A Mammalian Adaptor Protein with Coserved Src Homology 2 and Phosphotyrosine-binding Domains is Related to Shc and is Specifically Expressed in the Brain," *Proc. Natl. Acad. Sci. USA* 93: 2729-2734 (1996).

Oshima et al., "Targeted Disruption of the Cyclin-dependent Kinase 5 Gene Results in Abnormal Corticogenesis, Neuronal Pathology and Perinatal Death," *Proc. Natl. Acad. Sci. USA* 93: 11173-11178 (1996).

Selko, "Amyloid β-Protein and the Genetics of Alzheimer's Disease," *J. Biol. Chem.* 271: 18295-18298 (1996).

Sweet et al., "Scrambler, a New Neurological Mutation of the Mouse With Abnormalities of Neuronal Migration," *Mamm. Genome* 7: 798-802 (1996).

Zhou et al., "Structural Basis for IL-4 Receptor Phosphopeptide Recognition by the IRS-1 PTB Domain," *Nature Struct. Biol.* 3: 388-393 (1996).

Chae et al., "Mice Lacking p35, a Neuronal Specific Activator of Cdk5, Display Cortical Lamination Defects, Seizures, and Adult Lethality," *Neuron* 18: 29-42 (1997).

Del Rio et al., "A Role for Cajal-Retzius Cells and *reelin* in the Development of Hippocampal Connections," *Nature* 385: 70-74 (1997).

Howell et al., "Mouse Disabled (mDabl): a Src Binding Protein Implicated in Neuronal Development," *EMBO J.* 16: 121-132 (1997).

Sheldon et al., "*Scrambler* and *yotari* Disrupt the *disabled* Gene and Produce a *reeler*-like Phenotype in Mice," *Nature* 389: 730-733 (1997).

Soriano, "The PDGFα Receptor is Required for Neural Crest Cell Development and for Normal Patterning of the Somites," *Development* 124: 2691-2700 (1997).

Yoneshima et al., "A Novel Neurological Mutant Mouse, *yotari*, Which Exhibits *reeler*-like Phenotype but Expresses CR-50 Antigen/Reelin," *Neurosci. Res.* 29: 217-223 (1997).

* cited by examiner

SEQUENCE LISTING

```
<160> NUMBER OF SEQ ID NOS: 34

<210> SEQ ID NO 1
<211> LENGTH: 23
<212> TYPE: DNA
<213> ORGANISM: Artificial Sequence
<220> FEATURE:
<223> OTHER INFORMATION: DNA sequencing primer that hybridizes to pVP16
      vector

<400> SEQUENCE: 1
gcaagatctt agggatcgat tgg                                             23

<210> SEQ ID NO 2
<211> LENGTH: 2231
<212> TYPE: DNA
<213> ORGANISM: Mus dunni
<220> FEATURE:
<221> NAME/KEY: CDS
<222> LOCATION: (264)..(1931)
<223> OTHER INFORMATION:

<400> SEQUENCE: 2
cccagctcgg cgctcacccg ggcttccccg ggctggagag cgcgtttgag tgcggccgcc     60
cgcagggcat ggagagccgt gtcccgggcg gctgcggcag ccaaggagga tgctccgggg    120
gagccgagca ctccgccaga gtgaatgaca tgcacggtgt tgggtgtcct ttctgaaggg    180
aggagccttt ctcttggaga ggatcctcga tgagcctggc cgaggcccgg ggtctgtgtg    240
aagaggacta aggattaagt agg atg tca act gag aca gaa ctt caa gta gct    293
                         Met Ser Thr Glu Thr Glu Leu Gln Val Ala
                           1               5                  10 gtg aaa acc agc gcc aag aaa gac tcc agg aag aaa ggt cag gat cgc      341
Val Lys Thr Ser Ala Lys Lys Asp Ser Arg Lys Lys Gly Gln Asp Arg
             15                  20                  25 agc gaa gcc act ttg ata aag agg ttt aaa ggc gaa ggg gtc cgg tac      389
Ser Glu Ala Thr Leu Ile Lys Arg Phe Lys Gly Glu Gly Val Arg Tyr
         30                  35                  40 aaa gcc aag ctg att ggg att gat gaa gtg tcc gca gct cgg gga gac      437
Lys Ala Lys Leu Ile Gly Ile Asp Glu Val Ser Ala Ala Arg Gly Asp
     45                  50                  55 aag tta tgt caa gat tcc atg atg aag ctc aag ggt gtt gtt gct ggc      485
Lys Leu Cys Gln Asp Ser Met Met Lys Leu Lys Gly Val Val Ala Gly
 60                  65                  70 gca cgt tcc aag gga gaa cac aaa cag aaa atc ttt tta acc atc tcc      533
Ala Arg Ser Lys Gly Glu His Lys Gln Lys Ile Phe Leu Thr Ile Ser
 75                  80                  85                  90
```

-continued

| | | |
|---|---|---|
| ttt gga gga atc aaa atc ttt gat gag aag acg ggg gcc ctt cag cat<br>Phe Gly Gly Ile Lys Ile Phe Asp Glu Lys Thr Gly Ala Leu Gln His<br>                95                            100                      105 | 581 |
| cac cat gct gtt cat gaa att tcc tac att gcg aag gac atc aca gat<br>His His Ala Val His Glu Ile Ser Tyr Ile Ala Lys Asp Ile Thr Asp<br>           110                          115                              120 | 629 |
| cat cgg gct ttc gga tac gtt tgc ggg aag gaa ggg aat cac aga ttt<br>His Arg Ala Phe Gly Tyr Val Cys Gly Lys Glu Gly Asn His Arg Phe<br>               125                            130                          135 | 677 |
| gtg gcc atc aaa aca gcc cag gcg gct gaa cct gtt atc ctg gac ttg<br>Val Ala Ile Lys Thr Ala Gln Ala Ala Glu Pro Val Ile Leu Asp Leu<br>140                            145                            150 | 725 |
| aga gat ctc ttt caa ctc atc tat gag ctg aag caa aga gaa gaa ttg<br>Arg Asp Leu Phe Gln Leu Ile Tyr Glu Leu Lys Gln Arg Glu Glu Leu<br>155                            160                            165                      170 | 773 |
| gaa aaa aag gca caa aag gat aag cag tgt gaa caa gct gtg tac cag<br>Glu Lys Lys Ala Gln Lys Asp Lys Gln Cys Glu Gln Ala Val Tyr Gln<br>               175                            180                          185 | 821 |
| acc att ttg gaa gag gat gtg gaa gat ccc gtg tac cag tac att gtg<br>Thr Ile Leu Glu Glu Asp Val Glu Asp Pro Val Tyr Gln Tyr Ile Val<br>           190                          195                              200 | 869 |
| ttt gag gct gga cat gag cca atc cgt gat cct gaa aca gaa gag aac<br>Phe Glu Ala Gly His Glu Pro Ile Arg Asp Pro Glu Thr Glu Glu Asn<br>               205                            210                          215 | 917 |
| att tac cag gtt ccc acc agc caa aag aag gaa ggt gtt tat gat gtg<br>Ile Tyr Gln Val Pro Thr Ser Gln Lys Lys Glu Gly Val Tyr Asp Val<br>           220                          225                            230 | 965 |
| cca aaa agt caa cct gta agt gct gtg acc caa tta gaa ctt ttt gga<br>Pro Lys Ser Gln Pro Val Ser Ala Val Thr Gln Leu Glu Leu Phe Gly<br>235                            240                            245                      250 | 1013 |
| gac atg tcc acc cct cct gat ata acc tct ccc cct act cct gca acc<br>Asp Met Ser Thr Pro Pro Asp Ile Thr Ser Pro Pro Thr Pro Ala Thr<br>                     255                            260                          265 | 1061 |
| cca ggt gat gcc ttt ctc ccg tcg tcg tcc cag acg ctt ccg ggg agt<br>Pro Gly Asp Ala Phe Leu Pro Ser Ser Ser Gln Thr Leu Pro Gly Ser<br>           270                          275                            280 | 1109 |
| gca gat gtg ttt ggc tct atg tct ttc ggc act gct gct gta ccc tca<br>Ala Asp Val Phe Gly Ser Met Ser Phe Gly Thr Ala Ala Val Pro Ser<br>               285                            290                          295 | 1157 |
| ggt tat gtc gct atg ggc gcc gtc ctc cca tcc ttc tgg ggc cag cag<br>Gly Tyr Val Ala Met Gly Ala Val Leu Pro Ser Phe Trp Gly Gln Gln<br>300                            305                            310 | 1205 |
| ccc ctt gtt caa cag cag atc gcc atg ggt gct cag cca ccc gtc gct<br>Pro Leu Val Gln Gln Gln Ile Ala Met Gly Ala Gln Pro Pro Val Ala<br>315                            320                            325                      330 | 1253 |
| cag gtg ata cca gga gct cag ccc atc gca tgg ggc cag cca ggt ctc<br>Gln Val Ile Pro Gly Ala Gln Pro Ile Ala Trp Gly Gln Pro Gly Leu<br>               335                            340                          345 | 1301 |
| ttt cct gcc acc cag caa gcc tgg ccc act gtg gcc ggg cag ttc ccg<br>Phe Pro Ala Thr Gln Gln Ala Trp Pro Thr Val Ala Gly Gln Phe Pro<br>           350                          355                            360 | 1349 |
| cca gcc gcc ttc atg ccc aca caa act gtt atg cct tta gca gcc gcc<br>Pro Ala Ala Phe Met Pro Thr Gln Thr Val Met Pro Leu Ala Ala Ala<br>               365                            370                          375 | 1397 |
| atg ttc caa ggt ccc ctc acc ccc ctt gca acc gtc cca ggc acg aat<br>Met Phe Gln Gly Pro Leu Thr Pro Leu Ala Thr Val Pro Gly Thr Asn<br>380                            385                            390 | 1445 |
| gac tct gcc agg tca agt cca cag agt gac aag ccc agg cag aaa atg<br>Asp Ser Ala Arg Ser Ser Pro Gln Ser Asp Lys Pro Arg Gln Lys Met | 1493 |

-continued

```
                395                 400                 405                 410
ggg aag gag tct ttc aag gat ttc cag atg gtc cag cct cca ccc gta     1541
Gly Lys Glu Ser Phe Lys Asp Phe Gln Met Val Gln Pro Pro Pro Val
                    415                 420                 425 ccc tcc cgg aag cct gac cag ccc tcc ctg acc tgt acc tca gag gcc     1589
Pro Ser Arg Lys Pro Asp Gln Pro Ser Leu Thr Cys Thr Ser Glu Ala
                430                 435                 440 ttc tcc agt tac ttc aac aaa gtc ggg gtg gca cag gat aca gac gac     1637
Phe Ser Ser Tyr Phe Asn Lys Val Gly Val Ala Gln Asp Thr Asp Asp
            445                 450                 455 tgt gat gac ttt gac atc tcc caa ctg aac ttg acc cct gtg act tct     1685
Cys Asp Asp Phe Asp Ile Ser Gln Leu Asn Leu Thr Pro Val Thr Ser
        460                 465                 470 acc aca cca tct acc aac tca cct cca acc cca gcc cct agg cag agc     1733
Thr Thr Pro Ser Thr Asn Ser Pro Pro Thr Pro Ala Pro Arg Gln Ser
475                 480                 485                 490 tct cca tcc aaa tca tca gca tcc cac gtc agt gac ccg acc gca gat     1781
Ser Pro Ser Lys Ser Ser Ala Ser His Val Ser Asp Pro Thr Ala Asp
                    495                 500                 505 gac atc ttc gaa gaa ggc ttt gaa agt ccc agc aaa agt gaa gaa caa     1829
Asp Ile Phe Glu Glu Gly Phe Glu Ser Pro Ser Lys Ser Glu Glu Gln
                510                 515                 520 gaa gca cct gat gga tca cag gcc tcc tcc acc agt gat cca ttt ggg     1877
Glu Ala Pro Asp Gly Ser Gln Ala Ser Ser Thr Ser Asp Pro Phe Gly
            525                 530                 535 gag ccc agt ggt gag ccc agt ggt gat aat ata agt cca caa gac ggt     1925
Glu Pro Ser Gly Glu Pro Ser Gly Asp Asn Ile Ser Pro Gln Asp Gly
        540                 545                 550 agc tag atagcgcagg tctgggagcc agagcctctc tatgcgaaaa tcaacagacc      1981
Ser
555 taagaaatag catcaatgcg agctcatggt gggtgcttca cggatggcat gggaatctgc   2041 agtacaacag gctctcttgg gctctcacct cacttcatcc cacagaaaaa ctcacagtcg   2101 cccagtgaaa ccacctgaag aaggaacaac atggtttttg caaccaatg gcagatacct    2161 atggcagcac aaaacaaaaa acaaacaaaa caaaacacaa caacccacaa aagtacttaa   2221 aaaaaaaaaa                                                          2231

<210> SEQ ID NO 3
<211> LENGTH: 555
<212> TYPE: PRT
<213> ORGANISM: Mus dunni

<400> SEQUENCE: 3

Met Ser Thr Glu Thr Glu Leu Gln Val Ala Val Lys Thr Ser Ala Lys
1               5                   10                  15

Lys Asp Ser Arg Lys Lys Gly Gln Asp Arg Ser Glu Ala Thr Leu Ile
            20                  25                  30

Lys Arg Phe Lys Gly Glu Gly Val Arg Tyr Lys Ala Lys Leu Ile Gly
        35                  40                  45

Ile Asp Glu Val Ser Ala Ala Arg Gly Asp Lys Leu Cys Gln Asp Ser
    50                  55                  60

Met Met Lys Leu Lys Gly Val Val Ala Gly Ala Arg Ser Lys Gly Glu
65                  70                  75                  80

His Lys Gln Lys Ile Phe Leu Thr Ile Ser Phe Gly Gly Ile Lys Ile
                85                  90                  95

Phe Asp Glu Lys Thr Gly Ala Leu Gln His His His Ala Val His Glu
```

-continued

```
                100                 105                 110
Ile Ser Tyr Ile Ala Lys Asp Ile Thr Asp His Arg Ala Phe Gly Tyr
            115                 120                 125
Val Cys Gly Lys Glu Gly Asn His Arg Phe Val Ala Ile Lys Thr Ala
            130                 135                 140
Gln Ala Ala Glu Pro Val Ile Leu Asp Leu Arg Asp Leu Phe Gln Leu
145                 150                 155                 160
Ile Tyr Glu Leu Lys Gln Arg Glu Glu Leu Glu Lys Lys Ala Gln Lys
                165                 170                 175
Asp Lys Gln Cys Glu Gln Ala Val Tyr Gln Thr Ile Leu Glu Glu Asp
            180                 185                 190
Val Glu Asp Pro Val Tyr Gln Tyr Ile Val Phe Glu Ala Gly His Glu
            195                 200                 205
Pro Ile Arg Asp Pro Glu Thr Glu Glu Asn Ile Tyr Gln Val Pro Thr
            210                 215                 220
Ser Gln Lys Lys Glu Gly Val Tyr Asp Val Lys Ser Gln Pro Val
225                 230                 235                 240
Ser Ala Val Thr Gln Leu Glu Leu Phe Gly Asp Met Ser Thr Pro Pro
            245                 250                 255
Asp Ile Thr Ser Pro Pro Thr Pro Ala Thr Pro Gly Asp Ala Phe Leu
            260                 265                 270
Pro Ser Ser Ser Gln Thr Leu Pro Gly Ser Ala Asp Val Phe Gly Ser
            275                 280                 285
Met Ser Phe Gly Thr Ala Ala Val Pro Ser Gly Tyr Val Ala Met Gly
            290                 295                 300
Ala Val Leu Pro Ser Phe Trp Gly Gln Gln Pro Leu Val Gln Gln Gln
305                 310                 315                 320
Ile Ala Met Gly Ala Gln Pro Pro Val Ala Gln Val Ile Pro Gly Ala
            325                 330                 335
Gln Pro Ile Ala Trp Gly Gln Pro Gly Leu Phe Pro Ala Thr Gln Gln
            340                 345                 350
Ala Trp Pro Thr Val Ala Gly Gln Phe Pro Pro Ala Ala Phe Met Pro
            355                 360                 365
Thr Gln Thr Val Met Pro Leu Ala Ala Ala Met Phe Gln Gly Pro Leu
            370                 375                 380
Thr Pro Leu Ala Thr Val Pro Gly Thr Asn Asp Ser Ala Arg Ser Ser
385                 390                 395                 400
Pro Gln Ser Asp Lys Pro Arg Gln Lys Met Gly Lys Glu Ser Phe Lys
                405                 410                 415
Asp Phe Gln Met Val Gln Pro Pro Val Pro Ser Arg Lys Pro Asp
            420                 425                 430
Gln Pro Ser Leu Thr Cys Thr Ser Glu Ala Phe Ser Ser Tyr Phe Asn
            435                 440                 445
Lys Val Gly Val Ala Gln Asp Thr Asp Cys Asp Asp Phe Asp Ile
            450                 455                 460
Ser Gln Leu Asn Leu Thr Pro Val Thr Ser Thr Thr Pro Ser Thr Asn
465                 470                 475                 480
Ser Pro Pro Thr Pro Ala Pro Arg Gln Ser Ser Pro Ser Lys Ser Ser
                485                 490                 495
Ala Ser His Val Ser Asp Pro Thr Ala Asp Ile Phe Glu Glu Gly
            500                 505                 510
Phe Glu Ser Pro Ser Lys Ser Glu Glu Gln Glu Ala Pro Asp Gly Ser
            515                 520                 525
```

```
Gln Ala Ser Ser Thr Ser Asp Pro Phe Gly Glu Pro Ser Gly Glu Pro
    530                 535                 540
Ser Gly Asp Asn Ile Ser Pro Gln Asp Gly Ser
545                 550                 555

<210> SEQ ID NO 4
<211> LENGTH: 2663
<212> TYPE: DNA
<213> ORGANISM: Mus dunni
<220> FEATURE:
<221> NAME/KEY: CDS
<222> LOCATION: (264)..(917)
<223> OTHER INFORMATION:

<400> SEQUENCE: 4
cccagctcgg cgctcacccg ggcttccccg ggctggagag cgcgtttgag tgcggccgcc      60
cgcagggcat ggagagccgt gtcccgggcg gctgcggcag ccaaggagga tgctccgggg     120
gagccgagca ctccgccaga gtgaatgaca tgcacggtgt tgggtgtcct ttctgaaggg     180
aggagccttt ctcttggaga ggatcctcga tgagcctggc cgaggcccgg ggtctgtgtg     240
aagaggacta aggattaagt agg atg tca act gag aca gaa ctt caa gta gct     293
                         Met Ser Thr Glu Thr Glu Leu Gln Val Ala
                          1               5                  10 gtg aaa acc agc gcc aag aaa gac tcc agg aag aaa ggt cag gat cgc     341
Val Lys Thr Ser Ala Lys Lys Asp Ser Arg Lys Lys Gly Gln Asp Arg
             15                  20                  25 agc gaa gcc act ttg ata aag agg ttt aaa ggc gaa ggg gtc cgg tac     389
Ser Glu Ala Thr Leu Ile Lys Arg Phe Lys Gly Glu Gly Val Arg Tyr
         30                  35                  40 aaa gcc aag ctg att ggg att gat gaa gtg tcc gca gct cgg gga gac     437
Lys Ala Lys Leu Ile Gly Ile Asp Glu Val Ser Ala Ala Arg Gly Asp
     45                  50                  55 aag tta tgt caa gat tcc atg atg aag ctc aag ggt gtt gtt gct ggc     485
Lys Leu Cys Gln Asp Ser Met Met Lys Leu Lys Gly Val Val Ala Gly
 60                  65                  70 gca cgt tcc aag gga gaa cac aaa cag aaa atc ttt tta acc atc tcc     533
Ala Arg Ser Lys Gly Glu His Lys Gln Lys Ile Phe Leu Thr Ile Ser
 75                  80                  85                  90 ttt gga gga atc aaa atc ttt gat gag aag acg ggg gcc ctt cag cat     581
Phe Gly Gly Ile Lys Ile Phe Asp Glu Lys Thr Gly Ala Leu Gln His
                 95                 100                 105 cac cat gct gtt cat gaa att tcc tac att gcg aag gac atc aca gat     629
His His Ala Val His Glu Ile Ser Tyr Ile Ala Lys Asp Ile Thr Asp
             110                 115                 120 cat cgg gct ttc gga tac gtt tgc ggg aag gaa ggg aat cac aga ttt     677
His Arg Ala Phe Gly Tyr Val Cys Gly Lys Glu Gly Asn His Arg Phe
         125                 130                 135 gtg gcc atc aaa aca gcc cag gcg gct gaa cct gtt atc ctg gac ttg     725
Val Ala Ile Lys Thr Ala Gln Ala Ala Glu Pro Val Ile Leu Asp Leu
     140                 145                 150 aga gat ctc ttt caa ctc atc tat gag ctg aag caa aga gaa gaa ttg     773
Arg Asp Leu Phe Gln Leu Ile Tyr Glu Leu Lys Gln Arg Glu Glu Leu
155                 160                 165                 170 gaa aaa aag gca caa aag gat aag cag tgt gaa caa gct gtg tac cag     821
Glu Lys Lys Ala Gln Lys Asp Lys Gln Cys Glu Gln Ala Val Tyr Gln
                 175                 180                 185 acc att ttg gaa gag gat gtg gaa gat ccc gtg tac cag tac att gtg     869
Thr Ile Leu Glu Glu Asp Val Glu Asp Pro Val Tyr Gln Tyr Ile Val
             190                 195                 200
```

| ttt gag gct gga cat gag cca atc cgt gat cct gaa aca gaa gag aac | 917 |
| Phe Glu Ala Gly His Glu Pro Ile Arg Asp Pro Glu Thr Glu Glu Asn | |
| 205 210 215 | |
| atttaccagg ttcccaccag ccaaaagaag gaaggtgttt atgatgtgcc aaaaagtcaa | 977 |
| cctgtaagtt cacttgttca agcccagca gcagagagag cagaggcaga gtctcgaacc | 1037 |
| ggcccagctg agcctggctc aatcctccgt cctttagggt agatttacca ggttcccacc | 1097 |
| agccaaaaga aggaaggtgt ttatgatgtg ccaaaaagtc aacctgtaag ttcacttgtt | 1157 |
| caaagcccag cagcagagag agcagaggca gagtctcgaa ccggcccagc tgagcctggc | 1217 |
| tcaatcctcc gtcctttagg gtagccagga gtgagtcctg aaaccattct tgaggaattt | 1277 |
| atccatctac ccatcaagca tttatcgttc atctattcca cggagattgt tgaatggctc | 1337 |
| ctgtgtgtca ggcactgtgg taaagacagg aggcttacaa gtcagcccac gttccttctt | 1397 |
| aaagccaggt ctccttccat ggctgtgacc caattagaac ttttggaga catgtccacc | 1457 |
| cctcctgata taacctctcc ccctactcct gcaaccccag gtgatgcctt tctcccgtcg | 1517 |
| tcgtcccaga cgcttccggg gagtgcagat gtgtttggct ctatgtcttt cggcactgct | 1577 |
| gctgtaccct caggttatgt cgctatgggc gccgtcctcc catccttctg gggccagcag | 1637 |
| ccccttgttc aacagcagat cgccatgggt gctcagccac ccgtcgctca ggtgatacca | 1697 |
| ggagctcagc ccatcgcatg gggccagcca ggtctctttc ctgccaccca gcaagcctgg | 1757 |
| cccactgtgg ccgggcagtt cccgccagcc gccttcatgc ccacacaaac tgttatgcct | 1817 |
| ttagcagccg ccatgttcca aggtcccctc acccccttg caaccgtccc aggcacgaat | 1877 |
| gactctgcca ggtcaagtcc acagagtgac aagcccaggc agaaaatggg gaaggagtct | 1937 |
| ttcaaggatt tccagatggt ccagcctcca cccgtaccct cccggaagcc tgaccagccc | 1997 |
| tccctgacct gtacctcaga ggccttctcc agttacttca caaagtcgg ggtggcacag | 2057 |
| gatacagacg actgtgatga ctttgacatc tcccaactga acttgacccc tgtgacttct | 2117 |
| accacaccat ctaccaactc acctccaacc ccagccccta ggcagagctc tccatccaaa | 2177 |
| tcatcagcat cccacgtcag tgaccccacc gcagatgaca tcttcgaaga aggctttgaa | 2237 |
| agtcccagca aaagtgtaga acaagaagca cctgatggat cacaggcctc ctccaccagt | 2297 |
| gatccatttg gggagcccag tggtgagccc agtggtgata atataagtcc acaagacggt | 2357 |
| agctagatag cgcaggtctg ggagccagag cctctctatg cgaaaatcaa cagacctaag | 2417 |
| aaatagcatc aatgcgagct catggtgggt gcttcacgga tggcatggga atctgcagta | 2477 |
| caacaggctc tcttgggctc tcacctcact tcatcccaca gaaaaactca cagtcgccca | 2537 |
| gtgaaaccac ctgaagaagg aacaacatgg ttttttggcaa ccaatggcag ataccctatgg | 2597 |
| cagcacaaaa caaaaaacaa acaaaacaaa acacaacaac ccacaaaagt acttaaaaaa | 2657 |
| aaaaaa | 2663 |

<210> SEQ ID NO 5
<211> LENGTH: 218
<212> TYPE: PRT
<213> ORGANISM: Mus dunni

<400> SEQUENCE: 5

Met Ser Thr Glu Thr Glu Leu Gln Val Ala Val Lys Thr Ser Ala Lys
1               5                   10                  15

Lys Asp Ser Arg Lys Lys Gly Gln Asp Arg Ser Glu Ala Thr Leu Ile
            20                  25                  30

Lys Arg Phe Lys Gly Glu Gly Val Arg Tyr Lys Ala Lys Leu Ile Gly

-continued

```
                    35                  40                  45
Ile Asp Glu Val Ser Ala Ala Arg Gly Asp Lys Leu Cys Gln Asp Ser
 50                  55                  60

Met Met Lys Leu Lys Gly Val Ala Gly Ala Arg Ser Lys Gly Glu
 65                  70                  75                  80

His Lys Gln Lys Ile Phe Leu Thr Ile Ser Phe Gly Gly Ile Lys Ile
                 85                  90                  95

Phe Asp Glu Lys Thr Gly Ala Leu Gln His His Ala Val His Glu
                100                 105                 110

Ile Ser Tyr Ile Ala Lys Asp Ile Thr Asp His Arg Ala Phe Gly Tyr
                115                 120                 125

Val Cys Gly Lys Glu Gly Asn His Arg Phe Val Ala Ile Lys Thr Ala
130                 135                 140

Gln Ala Ala Glu Pro Val Ile Leu Asp Leu Arg Asp Leu Phe Gln Leu
145                 150                 155                 160

Ile Tyr Glu Leu Lys Gln Arg Glu Glu Leu Glu Lys Lys Ala Gln Lys
                165                 170                 175

Asp Lys Gln Cys Glu Gln Ala Val Tyr Gln Thr Ile Leu Glu Glu Asp
                180                 185                 190

Val Glu Asp Pro Val Tyr Gln Tyr Ile Val Phe Glu Ala Gly His Glu
                195                 200                 205

Pro Ile Arg Asp Pro Glu Thr Glu Glu Asn
        210                 215
```

<210> SEQ ID NO 6
<211> LENGTH: 1126
<212> TYPE: DNA
<213> ORGANISM: Mus dunni
<220> FEATURE:
<221> NAME/KEY: CDS
<222> LOCATION: (264)..(917)
<223> OTHER INFORMATION:

<400> SEQUENCE: 6

```
cccagctcgg cgctcacccg ggcttccccg ggctggagag cgcgtttgag tgcggccgcc      60
cgcagggcat ggagagccgt gtcccgggcg gctgcggcag ccaaggagga tgctccgggg     120
gagccgagca ctccgccaga gtgaatgaca tgcacggtgt tgggtgtcct ttctgaaggg     180
aggagccttt ctcttggaga ggatcctcga tgagcctggc cgaggcccgg gtctgtgtg      240 aagaggacta aggattaagt agg atg tca act gag aca gaa ctt caa gta gct     293
                       Met Ser Thr Glu Thr Glu Leu Gln Val Ala
                         1               5                  10 gtg aaa acc agc gcc aag aaa gac tcc agg aag aaa ggt cag gat cgc      341
Val Lys Thr Ser Ala Lys Lys Asp Ser Arg Lys Lys Gly Gln Asp Arg
             15                  20                  25 agc gaa gcc act ttg ata aag agg ttt aaa ggc gaa ggg gtc cgg tac      389
Ser Glu Ala Thr Leu Ile Lys Arg Phe Lys Gly Glu Gly Val Arg Tyr
         30                  35                  40 aaa gcc aag ctg att ggg att gat gaa gtg tcc gca gct cgg gga gac      437
Lys Ala Lys Leu Ile Gly Ile Asp Glu Val Ser Ala Ala Arg Gly Asp
     45                  50                  55 aag tta tgt caa gat tcc atg atg aag ctc aag ggt gtt gtt gct ggc      485
Lys Leu Cys Gln Asp Ser Met Met Lys Leu Lys Gly Val Val Ala Gly
 60                  65                  70 gca cgt tcc aag gga gaa cac aaa cag aaa atc ttt tta acc atc tcc      533
Ala Arg Ser Lys Gly Glu His Lys Gln Lys Ile Phe Leu Thr Ile Ser
 75                  80                  85                  90
```

```
ttt gga gga atc aaa atc ttt gat gag aag acg ggg gcc ctt cag cat      581
Phe Gly Gly Ile Lys Ile Phe Asp Glu Lys Thr Gly Ala Leu Gln His
                 95                 100                 105 cac cat gct gtt cat gaa att tcc tac att gcg aag gac atc aca gat      629
His His Ala Val His Glu Ile Ser Tyr Ile Ala Lys Asp Ile Thr Asp
            110                 115                 120 cat cgg gct ttc gga tac gtt tgc ggg aag gaa ggg aat cac aga ttt      677
His Arg Ala Phe Gly Tyr Val Cys Gly Lys Glu Gly Asn His Arg Phe
        125                 130                 135 gtg gcc atc aaa aca gcc cag gcg gct gaa cct gtt atc ctg gac ttg      725
Val Ala Ile Lys Thr Ala Gln Ala Ala Glu Pro Val Ile Leu Asp Leu
    140                 145                 150 aga gat ctc ttt caa ctc atc tat gag ctg aag caa aga gaa gaa ttg      773
Arg Asp Leu Phe Gln Leu Ile Tyr Glu Leu Lys Gln Arg Glu Glu Leu
155                 160                 165                 170 gaa aaa aag gca caa aag gat aag cag tgt gaa caa gct gtg tac cag      821
Glu Lys Lys Ala Gln Lys Asp Lys Gln Cys Glu Gln Ala Val Tyr Gln
                175                 180                 185 acc att ttg gaa gag gat gtg gaa gat ccc gtg tac cag gta att tct      869
Thr Ile Leu Glu Glu Asp Val Glu Asp Pro Val Tyr Gln Val Ile Ser
            190                 195                 200 gaa cca cgt cag ggt ttt gca tgc agc tgt gaa ggc tct ttt gac tga      917
Glu Pro Arg Gln Gly Phe Ala Cys Ser Cys Glu Gly Ser Phe Asp
        205                 210                 215 aacttgagga ttctgttgaa cgcagaacct gcagaagaat taagatgatt tctgaaggcc    977
agggttgcca gcctctgcag ggagagaatt tttccacact aagaagccag cagccgtgat   1037
gggagatcta gaaatccact tccttcttcg taccettgct tcagacccct ccccaatctg   1097
gaaagtttta tcctagaaat aaatgtttt                                     1126

<210> SEQ ID NO 7
<211> LENGTH: 217
<212> TYPE: PRT
<213> ORGANISM: Mus dunni

<400> SEQUENCE: 7

Met Ser Thr Glu Thr Glu Leu Gln Val Ala Val Lys Thr Ser Ala Lys
1               5                   10                  15

Lys Asp Ser Arg Lys Lys Gly Gln Asp Arg Ser Glu Ala Thr Leu Ile
            20                  25                  30

Lys Arg Phe Lys Gly Glu Gly Val Arg Tyr Lys Ala Lys Leu Ile Gly
        35                  40                  45

Ile Asp Glu Val Ser Ala Ala Arg Gly Asp Lys Leu Cys Gln Asp Ser
    50                  55                  60

Met Met Lys Leu Lys Gly Val Val Ala Gly Ala Arg Ser Lys Gly Glu
65                  70                  75                  80

His Lys Gln Lys Ile Phe Leu Thr Ile Ser Phe Gly Gly Ile Lys Ile
                85                  90                  95

Phe Asp Glu Lys Thr Gly Ala Leu Gln His His Ala Val His Glu
            100                 105                 110

Ile Ser Tyr Ile Ala Lys Asp Ile Thr Asp His Arg Ala Phe Gly Tyr
        115                 120                 125

Val Cys Gly Lys Glu Gly Asn His Arg Phe Val Ala Ile Lys Thr Ala
    130                 135                 140

Gln Ala Ala Glu Pro Val Ile Leu Asp Leu Arg Asp Leu Phe Gln Leu
145                 150                 155                 160

Ile Tyr Glu Leu Lys Gln Arg Glu Glu Leu Glu Lys Lys Ala Gln Lys
```

```
                      165                 170                 175
Asp Lys Gln Cys Glu Gln Ala Val Tyr Gln Thr Ile Leu Glu Asp
            180                 185                 190

Val Glu Asp Pro Val Tyr Gln Val Ile Ser Glu Pro Arg Gln Gly Phe
        195                 200                 205

Ala Cys Ser Cys Glu Gly Ser Phe Asp
    210                 215

<210> SEQ ID NO 8
<211> LENGTH: 99
<212> TYPE: DNA
<213> ORGANISM: Mus dunni
<220> FEATURE:
<221> NAME/KEY: CDS
<222> LOCATION: (1)..(99)
<223> OTHER INFORMATION:

<400> SEQUENCE: 8 aat agc cag ccg ctg gag gat ttc gaa tcg cgc ttt gcc gca gcc acg      48
Asn Ser Gln Pro Leu Glu Asp Phe Glu Ser Arg Phe Ala Ala Ala Thr
1               5                   10                  15 ccg aac agg aac ctg tca atg gac ttt gat gag ctt ctc gag gca acc      96
Pro Asn Arg Asn Leu Ser Met Asp Phe Asp Glu Leu Leu Glu Ala Thr
            20                  25                  30 aag                                                                  99
Lys

<210> SEQ ID NO 9
<211> LENGTH: 33
<212> TYPE: PRT
<213> ORGANISM: Mus dunni

<400> SEQUENCE: 9

Asn Ser Gln Pro Leu Glu Asp Phe Glu Ser Arg Phe Ala Ala Ala Thr
1               5                   10                  15

Pro Asn Arg Asn Leu Ser Met Asp Phe Asp Glu Leu Leu Glu Ala Thr
            20                  25                  30

Lys

<210> SEQ ID NO 10
<211> LENGTH: 30
<212> TYPE: DNA
<213> ORGANISM: Artificial Sequence
<220> FEATURE:
<223> OTHER INFORMATION: PCR amplification primer

<400> SEQUENCE: 10
cgcggatccc atcaccatgc tgttcatgaa                                     30

<210> SEQ ID NO 11
<211> LENGTH: 29
<212> TYPE: DNA
<213> ORGANISM: Artificial Sequence
<220> FEATURE:
<223> OTHER INFORMATION: PCR amplification primer

<400> SEQUENCE: 11
cgcgaattcc gacgggagaa aggcatcac                                      29

<210> SEQ ID NO 12
<211> LENGTH: 28
<212> TYPE: DNA
<213> ORGANISM: Artificial Sequence
```

-continued

<220> FEATURE:
<223> OTHER INFORMATION: PCR amplification primer

<400> SEQUENCE: 12
cgcggatccg ccactttgat aaagaggt                                28

<210> SEQ ID NO 13
<211> LENGTH: 27
<212> TYPE: DNA
<213> ORGANISM: Artificial Sequence
<220> FEATURE:
<223> OTHER INFORMATION: PCR amplification primer

<400> SEQUENCE: 13
ccggaattcc acgggatctt ccacatc                                 27

<210> SEQ ID NO 14
<211> LENGTH: 20
<212> TYPE: PRT
<213> ORGANISM: Mus dunni

<400> SEQUENCE: 14

Cys Glu Leu Gln Val Ala Ala Ala Val Lys Thr Ser Ala Lys Lys Asp
1               5                  10                  15

Ser Arg Lys Lys
        20

<210> SEQ ID NO 15
<211> LENGTH: 17
<212> TYPE: PRT
<213> ORGANISM: Mus dunni

<400> SEQUENCE: 15

Cys Gly Glu Pro Pro Ser Gly Gly Asp Asn Ile Ser Pro Gln Asp Gly
1               5                  10                  15

Ser

<210> SEQ ID NO 16
<211> LENGTH: 30
<212> TYPE: DNA
<213> ORGANISM: Artificial Sequence
<220> FEATURE:
<223> OTHER INFORMATION: PCR amplification primer

<400> SEQUENCE: 16
ctcggatcct catggggagc agcaagagca                              30

<210> SEQ ID NO 17
<211> LENGTH: 28
<212> TYPE: DNA
<213> ORGANISM: Artificial Sequence
<220> FEATURE:
<223> OTHER INFORMATION: PCR amplification primer

<400> SEQUENCE: 17
ctcatgcatc ctataggttc tctccagg                                28

<210> SEQ ID NO 18
<211> LENGTH: 27
<212> TYPE: DNA
<213> ORGANISM: Artificial Sequence
<220> FEATURE:
<223> OTHER INFORMATION: PCR amplification primer

<400> SEQUENCE: 18
cgcggatcca ggatgtcaac tgagaca                          27

<210> SEQ ID NO 19
<211> LENGTH: 29
<212> TYPE: DNA
<213> ORGANISM: Mus abbotti

<400> SEQUENCE: 19
cgcggatcct tcactgggcg actgtgagt                        29

<210> SEQ ID NO 20
<211> LENGTH: 5
<212> TYPE: PRT
<213> ORGANISM: Artificial Sequence
<220> FEATURE:
<223> OTHER INFORMATION: PCR amplification primer
<220> FEATURE:
<221> NAME/KEY: MISC_FEATURE
<222> LOCATION: (4)..(4)
<223> OTHER INFORMATION: X = Any amino acid

<400> SEQUENCE: 20

Val Tyr Gln Xaa Ile
1               5

<210> SEQ ID NO 21
<211> LENGTH: 4
<212> TYPE: PRT
<213> ORGANISM: Mus dunni

<400> SEQUENCE: 21

Tyr Gln Tyr Ile
1

<210> SEQ ID NO 22
<211> LENGTH: 4
<212> TYPE: PRT
<213> ORGANISM: Mus dunni

<400> SEQUENCE: 22

Tyr Ile Tyr Val
1

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide for site directed mutagenesis

<400> SEQUENCE: 23
cacaatgaac tggaagacgg gatcttccac                       30

<210> SEQ ID NO 24
<211> LENGTH: 24
<212> TYPE: DNA
<213> ORGANISM: Artificial sequence
<220> FEATURE:
<223> OTHER INFORMATION: Oligonucleotide P2 for PCR genotyping

<400> SEQUENCE: 24
gtcaggcttc ctaagtagaa agga                             24

<210> SEQ ID NO 25
<211> LENGTH: 24

```
<212> TYPE: DNA
<213> ORGANISM: Artificial Sequence
<220> FEATURE:
<223> OTHER INFORMATION: Oligonucleotide P2 for PCR genotyping

<400> SEQUENCE: 25
ttccaggagc gaaatcactc aacc                                          24

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide P3 for PCR genotyping

<400> SEQUENCE: 26
gggaaaagcg cctcccctac ccggt                                         25

<210> SEQ ID NO 27
<211> LENGTH: 14
<212> TYPE: PRT
<213> ORGANISM: Artificial Sequence
<220> FEATURE:
<223> OTHER INFORMATION: Conserved PTB binding domain of APP, APLP1 and
      APLP2
<220> FEATURE:
<221> NAME/KEY: MISC_FEATURE
<222> LOCATION: (8)..(9)
<223> OTHER INFORMATION: X = Any amino acid
<220> FEATURE:
<221> NAME/KEY: MISC_FEATURE
<222> LOCATION: (11)..(14)
<223> OTHER INFORMATION: X = Any amino acid

<400> SEQUENCE: 27

Gly Tyr Glu Asn Pro Thr Tyr Xaa Xaa Glu Xaa Xaa Xaa Xaa
1               5                   10

<210> SEQ ID NO 28
<211> LENGTH: 7
<212> TYPE: PRT
<213> ORGANISM: Artificial Sequence
<220> FEATURE:
<223> OTHER INFORMATION: NPXY motif of LDL receptor related protein

<400> SEQUENCE: 28

Asn Phe Thr Asn Pro Val Tyr
1               5

<210> SEQ ID NO 29
<211> LENGTH: 7
<212> TYPE: PRT
<213> ORGANISM: NPXY motif of LDL receptor related protein

<400> SEQUENCE: 29

Asn Phe Asp Asn Pro Val Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: NPXY motif in peptides derived from p150 ship

<400> SEQUENCE: 30

Met Phe Glu Asn Pro Leu Tyr
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: NPXY motif in peptides derived from p150 ship

<400> SEQUENCE: 31

Glu Met Ile Asn Pro Asn Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: NPXY motif in peptides derived from EGF
      receptor

<400> SEQUENCE: 32

Ala Val Gly Asn Pro Glu Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: NPXY motif in peptides derived from TnKA

<400> SEQUENCE: 33

Ile Ile Glu Asn Pro Gln Tyr
1               5

<210> SEQ ID NO 34
<211> LENGTH: 7
<212> TYPE: PRT
<213> ORGANISM: Artificial Sequence
<220> FEATURE:
<223> OTHER INFORMATION: NPXY motif in peptides derived from insulin
      receptor

<400> SEQUENCE: 34

Ala Ser Ser Asn Pro Glu Tyr
1               5
```

ISOLATION AND EXPRESSION OF A DISABLED PROTEIN GENE MDAB1 AND METHODS

RELATED APPLICATIONS

The present application claims the benefit and is a continuation-in-part application of U.S. Provisional Ser. No. 60/056,473, filed Aug. 21, 1997, which is incorporated herein by reference.

GOVERNMENT SUPPORT

This work was supported by grants CA41097, CA41072, HD25326 and HD24875 from the National Institutes of Health. The U.S. Government may have certain rights in the invention.

BACKGROUND OF THE INVENTION

Numerous developmental processes are regulated by signaling cascades that alter protein phosphotyrosine levels. Many extracellular cues are linked to cellular responses via transmembrane receptor protein-tyrosine kinases (PTKs) and phosphatases (PTPs). In the nervous system, transmembrane kinases and phosphatases are required for neuronal differentiation and survival, neurite extension, the directed growth of the neuronal growth cone, and the fasciculation of nerve bundles (Snider, *Cell* 77:627-638 (1994); Callahan et al., *Nature* 376;171-174 (1995); Tessier-Lavigne, *Cell* 82:345-348 (1995); Desai et al., *Cell* 84:599-609 (1996); Krueger et al., *Cell* 84:611-622 (1996)). These transmembrane receptors are directly regulated by specific ligands. Cytoplasmic PTKs are also involved in the development of the nervous system, although the ligands which induce their activation are less well understood (Gertler et al., *Cell* 58:103-113 (1989); Grant et al., *Science* 258:1903-1910 (1992); Umemori et al., *Nature* 367:572-576 (1994)). There is growing evidence that these kinases are regulated in pathways responding to components of the extracellular milieu and may function to regulate axonal growth downstream of receptors that lack intrinsic kinase activity (Bixby & Harris, *Ann. Rev. Cell. Biol.* 7:117-159 (1991)).

The non-receptor PTK Src is highly expressed in the developing mammalian nervous system (Maness et al., *Adv. Exp. Med. & Biol.* 265:117-125, (1990); Maness, *Dev. Neurosci.* 14:257-270 (1992)). During neurogenesis Src kinase activity increases and Src becomes concentrated in growth cones of neurons. Growth cones migrate by extending actin-rich filopodia and lamellipodia, and tyrosine phosphorylation is important for the formation of these actin structures (Wu & Goldberg, *J. Cell Biol.* 123:653-664 1993; Goldberg & Wu, *J. Neurobiol.* 27:553-560 (1995)). Neurons cultured from mice that lack Src extend neurites less well than wild-type neurons when plated on surfaces coated with the neural cell adhesion molecule L1 (Ignelzi et al., *Neuron* 12:873-884 (1994)). This defect is specific, since neurons lacking the Src relatives Fyn or Yes extend neurites normally (Beggs et al., *J. Cell Biol.* 127:825-833 (1994)). Moreover, neurons from mice lacking Fyn extend only short neurites on NCAM-140 but extend long neurites on L1 (Beggs et al., ibid.). Src and Yes are not needed for neurite extension on NCAM-140. These specific defects point to the existence of adhesion-stimulated, Src- and Fyn-dependent, regulatory processes required for neurite extension. Signals from neurotrophin receptor PTKs, such as TrkA, may also be relayed through Src. Nerve growth factor-(NGF) induced neurite extension is Src dependent in PC12 pheochromocytoma cells (Kremer et al., *J. Cell Biol.* 115:809-819 (1991); Vaillancourt et al., *Mol. Cell. Biol.* 15:3644-3653 (1995)).

The non-receptor tyrosine kinase, Abl, participates in nervous system development in *Drosophila*. The *Drosophila* Abl (dAbl) protein is found in many cell types in the developing embryo, but expression is highest in the cell bodies and axons of neurons in the developing central nervous system (CNS) (Gertler et al., ibid. (1989); Bennett & Hoffmann, *Devel.* 116:953-966 (1992)). Flies lacking the dAbl gene develop past metamorphosis but die as adults before or soon after eclosion (Henkemeyer et al., *Cell* 51:821-828 (1987)). Five genes were identified in screens for dominant second site mutations that exacerbate the dabl⁻ phenotype and have been dubbed HDA (haploinsufficient, dependent upon dAbl) genes (Gertler et al., ibid., (1989); Hill et al., *Genetics* 141:595-606 (1995)). When heterozygous for a mutation in a HDA gene, dAbl⁻ but not dAbl⁺ embryos die as embryos, with a characteristic terminal phenotype. The neurons of the CNS are present in normal number and extend axons, but gaps are apparent in the commissural and longitudinal axon bundles (Gertler et al., ibid. (1989), Gertler et al., *Genes Dev.* 7:441-453 (1993); Hill et al., ibid. (1995)). Three of the HDA genes, disabled (dab), prospero, and fax have been cloned and have distinct properties (Vaessin et al., *Cell* 67:941-953 (1991); Gertler et al., ibid. (1993); Hill et al., ibid. (1995)). Homozygous mutations in the HDA genes dab and fax in a dAbl mutant background results in almost complete loss of CNS axonal tracts. The dab and fax genes also show dosage sensitive interactions with each other (Gertler, "Genetic Modifiers of the *Drosophila* abl mutant phenotype," Ph.D. Dissertation, University of Wisconsin-Madison (1992); Hill et al., ibid. (1995)) as well as with dAbl and therefore may have related functions.

The *Drosophila* dab gene encodes a 2412 residue protein (Dab) that co-localizes with dAbl to the cell bodies and axons of embryonic CNS neurons (Gertler et al., ibid. (1993)). In *Drosophila* Dab is essential for normal CNS development, even in the presence of dAbl. Dab is tyrosine phosphorylated in insect cells and, given the co-localization with dAbl in the CNS, it has been suggested that Dab may be a physiological substrate of dAbl (Gertler et al., ibid. (1993)). However, the role of tyrosine phosphorylation in regulating Dab function, and the identities of the PTKs that phosphorylate Dab, remain unclear. The kinase activity of dAbl is dispensable for normal embryonic development, unless the levels of Dab or other HDA gene products are reduced by heterozygous mutations (Henkemeyer et al., *Cell* 63:949-960 (1990)). Using a temperature-sensitive mutant, dAbl kinase activity was shown to be required in dab heterozygotes after the time of cell fate specification and during the time of axonogenesis in the embryonic CNS (Henkemeyer et al., ibid. (1990)). Despite the loss of nerve bundles in the CNS, the total number of neurons is unaffected (Gertler et al., *Science* 248:857-860 (1990)). These results suggest that dAbl has kinase dependent and independent roles in development. Other PTKs that are expressed in the fly CNS, such as *Drosophila* Src(dSrc) (Simon et al., *Cell* 42:831-840 (1985)), may substitute for the dAbl kinase requirement in CNS development, provided the levels of Dab are normal.

SUMMARY OF THE INVENTION mDab1, a mammalian homolog of Dab, is identified. mDab1 was cloned based upon its interaction with Src in a yeast two-hybrid screen. The mdab1 gene is expressed as a variety of spliced mRNAs in the nervous system and in some cell lines, and mDab1 proteins are differentially expressed and tyrosine phosphorylated during neural development. When phosphorylated on tyrosine, mDab1 binds to the SH2 domains of Src, Fyn and Abl. mDab1 also forms complexes with cellular phosphotyrosyl proteins through a phosphotyrosine-binding (PTB) domain. mDab1 appears to play a role as an adaptor protein that participates in development of the nervous system.

The present invention further demonstrates that disruption of the mammalian disabled1 (mdab1) gene disturbs neuronal layering in the cerebral cortex, hippocampus and cerebellum.

In further aspects of the invention, mDab1 proteins, peptides, fusion proteins and antibodies are used in a variety of screening and diagnostic methods.

DESCRIPTION OF THE SPECIFIC EMBODIMENTS

The present invention identifies a mammalian homolog of the *Drosophila* Disabled (Dab) protein, mDab1, and shows it is an adaptor molecule functioning in neural development. More specifically, the present invention provides representative nucleotide sequences encoding murine Dab1.

It is an object of the present invention to provide representative polynucleotide molecules and amino acids sequences encoding mDab1. Sequences encoding mDab1 include those sequences that are identical or result in minor variations in amino acid sequence, such as those due to genetic polymorphisms, differences between species and those in which blocks of amino acids have been added, altered or replaced without substantially altering the biological activity of the proteins.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, far nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

mDab1 of the present invention has been shown to comprise a phosphotyrosine binding domain and has been shown to be capable of binding to/or associating with SH2 domains of Src, Fyn and Abl. Further, the disclosed polynucleotide sequences or portions thereof can be used to identify and isolate mammalian Dab1 polynucleotide molecules from suitable hosts such as canine, ovine, bovine, caprine, lagomorph or the like. In particular, the nucleotide sequences encoding the phosphotyrosine binding domain can be used to identify polynucleotide molecules encoding mDab1. Complementary DNA molecules encoding mDab1 may be obtained by constructing a cDNA library from mRNA, for example, brain. DNA molecules encoding mDab1 may be isolated from such a library using the disclosed sequences in standard hybridization techniques (e.g., Sambrook et al. ibid., and Bothwell, Yancopoulos and Alt, eds, *Methods for Cloning and Analysis of Eukaryotic Genes*, Jones and Bartlett Publishers, Boston, Mass. 1990) or by amplification of sequences using polymerase chain reaction (PCR) amplification (e.g, Loh et al. *Science* 243: 217-222, 1989; Frohman et al., *Proc. Natl. Acad. Sci. USA* 85: 8998-9002, 1988; and Erlich (ed.), *PCR Technology: Principles and Applications for DNA Amplification*, Stockton Press, 1989; and U.S. Pat. No. 4,683,195, which are incorporated by reference herein in their entirety).

In a similar manner, genomic DNA encoding mDab1 is obtained using probes designed from the sequences disclosed herein. Suitable probes for use in identifying mDab1 sequences are obtained from mDab1-specific sequences that are highly conserved regions between murine and *Drosophila* Dab coding sequences. Upstream regulatory regions of mDab1 are obtained using the same methods. Suitable PCR primers are between 7-50 nucleotides in length, more preferably between 15 and 25 nucleotides in length. Alternatively, mDab1 polynucleotide molecules may be isolated using standard hybridization probes of at least about 7 nucleotides in length and up to and including the full coding sequence.

The choice of hybridization conditions will generally be guided by the purpose of the hybridization, the type of hybridization (DNA-DNA or DNA-RNA), and the level of relatedness between the sequences. Methods for hybridization are well established in the literature; See, for example: Sambrook, ibid.; Hames and Higgins, eds, *Nucleic Acid Hybridization A Practical Approach*, IRL Press, Washington D.C., 1985; Berger and Kimmel, eds, *Methods in Enzymology*, Vol. 52, Guide to Molecular Cloning Techniques, Academic Press Inc., New York, N.Y., 1987; and Bothwell, Yancopoulos and Alt, eds, *Methods for Cloning and Analysis of Eukaryotic Genes*, Jones and Bartlett Publishers, Boston, Mass. 1990; which are incorporated by reference herein in their entirety. The stability of nucleic acid duplexes will decrease with an increased number and location of mismatched bases; thus, the stringency of hybridization may be used to maximize or minimize the stability of such duplexes. Hybridization stringency can be altered by: adjusting the temperature of hybridization; adjusting the percentage of helix-destabilizing agents, such as formamide, in the hybridization mix; and adjusting the temperature and salt concentration of the wash solutions. In general, the stringency of hybridization is adjusted during the post-hybridization washes by varying the salt concentration and/or the temperature. Stringency of hybridization may be reduced by reducing the percentage of formamide in the hybridization solution or by decreasing the temperature of the wash solution. High stringency conditions may involve high temperature hybridization (e.g., 65-68° C. in aqueous solution containing 4-6×SSC, or 42° C. in 50% formamide) combined with washes at high temperature (e.g., 5-25° C. below the $T_m$) at a low salt concentration (e.g., 0.1×SSC). Reduced stringency conditions may involve lower hybridization temperatures (e.g., 35-42° C. in 20-50% formamide) with washes at intermediate temperature (e.g., 40-60° C.) and in a higher salt concentration (e.g., 2-6×SSC). Moderate stringency conditions may involve hybridization at a temperature between 50° C. and 55° C. and washes in 0.1×SSC, 0.1% SDS at between 50° C. and 55° C.

In an another method for isolating mDab related polynucleotide sequences, a modified yeast two-hybrid system can be used. This method provides that a library of cDNA from a cellular source is prepared and inserted into an expression that permits the expression of the inserted cDNA. A particularly preferred cellular source is brain or neuronal tissue. The prepared cDNA library is screened for binding to expressed Src proteins. For example, Src-Lex A fusion constructs can be prepared from wild type Src DNA. Clones containing inserts demonstrated to express proteins capable of binding to the Src containing fusion proteins are selected and the inserts isolated and analyzed for relatedness to the disclosed mDab1 polynucleotide sequences as disclosed herein.

The invention also provides isolated and purified polynucleotide molecules encoding mDab1 capable of hybridizing under stringent conditions to an oligonucleotide of 15 or more contiguous nucleotides of SEQ ID NO: 2, SEQ ID NO: 4, or SEQ ID NO: 6 and their complementary strands. The isolated mDab1 polynucleotide molecules preferably encode mDab1 proteins or fragments thereof that are capable of binding to Src- and Abl-related tyrosine kinases through their Src homology (SH) 2 domains and to other proteins through its protein-interacting PI/PTB domain.

The present invention also provide methods for producing recombinant mDab1 by inserting a DNA molecule encoding mDab1 into a suitable expression vector, which is in turn used to transfect or transform a suitable host cell. Suitable expression vectors for use in carrying out the present invention will generally comprise a promoter capable of directing the transcription of a polynucleotide molecule of interest in a host cell. Representative expression vectors may include both plasmid and/or viral vector sequences. Suitable vectors include retroviral vectors, vaccinia viral vectors, CMV viral vectors, BLUESCRIPT, baculovirus vectors, and the like. Promoters capable of directing the transcription of a cloned gene or cDNA may be inducible or constitutive promoters and include viral and cellular promoters. For expression in mammalian host cells, suitable viral promoters include the immediate early cytomegalovirus promoter (Boshart et al., *Cell* 41: 521-530, 1985) and the SV40 promoter (Subramani et al., *Mol. Cell. Biol.* 1: 854-864, 1981). Suitable cellular promoters for expression of proteins in mammalian host cells include but are not limited to the mouse metallothionien-1 promoter (Palmiter et al., U.S. Pat. No. 4,579,821), and tetracycline-responsive promoter (Gossen and Bujard, *Proc. Natl. Acad. Sci. USA* 89: 5547-5551, 1992 and Pescini et al., *Biochem. Biophys. Res. Comm.* 202: 1664-1667, 1994). Also contained in the expression vectors is a transcription termination signal located downstream of the coding sequence of interest. Suitable transcription termination signals include the early or late polyadenylation signals from SV40 (Kaufman and Sharp, *Mol. Cell. Biol.* 2:1304-1319, 1982), the polyadenylation signal from the Adenovirus 5 e1B region and the human growth hormone gene terminator (DeNoto et al., *Nucleic Acid. Res.* 9: 3719-3730, 1981).

Mammalian cells may be transfected by a number of methods including calcium phosphate precipitation (Wigler et al., *Cell* 14: 725, 1978; Corsaro and Pearson, *Somatic Cell Genetics* 7: 603, 1981; Graham and Van der Eb, *Virology* 52: 456, 1973); lipofection (Felgner et al., *Proc. Natl. Acad. Sci. USA* 84: 7413-7417, 1987), microinjection and electroporation (Neumann et al., *EMBO J.* 1: 8410845, 1982). Mammalian cells can be transduced with virus such as SV40, CMV and the like. In the case of viral vectors, cloned DNA molecules may be introduced by infection of susceptible cells with viral particles. Retroviral vectors may be preferred for use in expressing mDab1 in mammalian cells.

It may be preferable to use a selectable marker to identify cells that contain the cloned DNA. Selectable markers are generally introduced into the cells along with the cloned DNA molecules and include genes that confer resistance to drugs, such as neomycin, hygromycin and methotrexate. Selectable markers may also complement auxotrophies in the host cell. Yet other selectable markers provide detectable signals, such as beta-galactosidase to identify cells containing the cloned DNA molecules. Selectable markers may be amplifiable. Such amplifiable selectable markers may be used to amplify the number of sequences integrated into the host genome.

As would be evident to one of ordinary skill in the art, the polynucleotide molecules of the present invention may be expressed *Saccharomyces cerevisiae*, filamentous fungi, and *E. coli*. Methods for expressing cloned genes in *Saccharomyces cerevisiae* are generally known in the art (see, "Gene Expression Technology," *Methods in Enzymology, Vol.* 185, Goeddel (ed.), Academic Press, San Diego, Calif., 1990 and "Guide to Yeast Genetics and Molecular Biology," *Methods in Enzymology*, Guthrie and Fink (eds.), Academic Press, San Diego, Calif., 1991; which are incorporated herein by reference). Filamentous fungi (e.g., strains of *Aspergillus*) may also be used to express the proteins of the present invention. Methods for expressing genes and cDNAs in cultured mammalian cells and in *E. coli* is discussed in detail in Sambrook et al. (*Molecular Cloning: A Laboratory Manual*, Second Edition, Cold Spring Harbor, N.Y., 1989; which is incorporated herein by reference). As would be evident to one skilled in the art, one could express the protein of the instant invention in other host cells such as avian, insect and plant cells using regulatory sequences, vectors and methods well established in the literature.

Dab is implicated in establishing axonal connections in the *Drosophila* embryonic CNS, in collaboration with one or more tyrosine kinases (Gertler et al., ibid. (1989)). mDab1 shares several characteristics with *Drosophila* Dab. The mdab1 gene is alternatively spliced to create several mRNAs and proteins with common amino-termini. This region is most highly conserved across the Dab family and contains a predicted PTB. mDab1 is expressed in certain neuronal and hematopoietic cell lines and is localized to the growing nerves of embryonic mice. mdab1 encodes a tyrosine-phosphorylated cytoplasmic protein, p80, that binds to Src- and Abl-related tyrosine kinases through their Src homology (SH) 2 domains and to other proteins through its protein-interacting PI/PTB domain (Howell et al., *EMBO J.* 16:1165-1175 (1997) and Margolis, *J. Lab. Clin. Med.* 128:235-241 (1996)). There are parallels in the development of neurons and hematopoietic cells, and a number of other genes are similarly restricted in expression (Anderson, *Neuron* 3:1-12 (1989)). During mouse embryogenesis, mDab1 is tyrosine phosphorylated when the nervous system is undergoing dramatic expansion. Another Dab relative, known as p96 or mDab2 in the mouse (Xu et al., ibid. (1995)) and DOC-2 in humans (Albertsen et al., ibid. (1996)), has been reported. The mdab2 gene is also alternatively spliced, but it appears to be widely expressed, and there is no evidence for tyrosine phosphorylation or association with tyrosine phosphorylated proteins.

Tyrosine phosphorylated mDab1 associates with the SH2 domains of Src, Fyn and Abl. As disclosed in more detail herein, mDab1 and Src interact when P19 embryonal carcinoma (EC) cells undergo differentiation into neuronal cell types, and mDab-Src complexes are formed when mDab1 is overexpressed in fibroblasts transformed by activated mutant Src. Moreover, mDab1 p60 and p80 proteins form complexes with Src after induction of P19 cell differentiation along neuronal lineages. The tyrosine phosphorylation and therefore potential for subsequent SH2 domain interaction is developmentally regulated. Ligands for the Src SH2 domain may activate Src by competition for an intramolecular repressive interaction (Brown & Cooper, *Biochim. Biophys. Acta* 1287:121-149 (1996)). mDab1 p80 may act in this way, and may induce Src activation when mDab1 is phosphorylated by upstream kinases that do not activate Src directly. Differential splicing of mDab1 creates proteins containing distinct potential tyrosine phosphorylation sites.

mDab1 can form complexes with cellular phosphotyrosyl proteins through a domain that is related to the PTB domains of the Shc family of adaptor proteins. The importance of the mDab1 PTB is suggested by its conservation across the Dab family, but it is sufficiently divergent in sequence from the Shc family of PTBs to question whether it adopts a similar structure. PTBs are difficult to recognize by primary sequence alone. The IRS-1 PTB, for example, is highly divergent in primary sequence, yet is fully functional and has a similar structure to the ShcA PTB (Zhou et al., ibid. (1996)). PTBs can bind to phosphotyrosyl peptides and to polyphosphoinositides (Zhou et al., ibid. (1995)). Peptides containing the Asn Pro Xaa pTyr (NPXpY) consensus sequence bind to the ShcA. However, some PTB domains have been discovered that can bind non-phosphorylated proteins. The brain proteins FE65 and X11, for example, have PTB domains that bind a non-phosphorylated sequence, Asn Pro Xaa Tyr present in the amyloid precursor protein. The molecular structure of the X11 PTB domain with the non-phosphorylated peptide bound shows many similarities with the Shc and IRS-1 PTR domains. The PTB domain of Numb was shown to bind to a non-phosphorylated or phosphorylated peptide lacking an Asn Pro Xaa Tyr (NPXY) sequence, and the Shc PTB domain was found to bind to a non-phosphorylated Asn Pro Xaa His (NPXH) peptide.

Sequence conservation in the mDab1 PTB is too low to predict whether it binds phosphoinositides, but it appears, as detailed herein, to bind to phosphotyrosine containing proteins of 200, 120, 50-65 and 40 kDa from extracts of embryonic mouse heads. Since the mDab1 PTB domain is the most highly conserved part of the protein, the identification of the ligands may be central to understanding mdab1 function.

Using the mDab1 PTB domain as the "bait" in a yeast-two hybrid screen, a brain cDNA-LexA fusion library was screened for proteins that bind the mDab1 PTB. A comprehensive screen for mDab1 PTB protein ligands showed that Tyr or Phe Xaa Asn Pro Xaa Tyr (Y/FXNPXY) sequences found in the amyloid precursor protein (APP), its relatives ALP1 and ALP2, the LDL receptor related protein (LRP)/α2 macroglobulin receptor and Ship are high affinity ligands for the mDab1 PTB domain. APP, ALP1, ALP2, and LRP are all expressed in the developing embryonic brain, when mDab1 function is important.

The beta amyloid precursor protein (APP) is expressed as five spliced forms, all of which are transmembrane proteins. All of the splice forms have a C-terminal tail. The shortest major isoform of 165 amino acids is expressed almost exclusively in neurons and the other two major forms of 770 and 751 amino acids are expressed in both neural and non-neural cells. Abnormal cleavage of APP results in the production small peptides that lead to Alzheimer's disease (for review, see Zheng et al., *Cell* 81:525-531 (1995) and Selkoe, *J. Biol. Chem.* 271:18295-18298 (1996); which are incorporated herein by reference). The major constituent of Alzheimer's plaques is a 38-43 amino acid peptide (amyloid β-protein (Aβ)). APP is transported to the cell surface where it is either cleaved by proteolysis or endocytosed. Endocytosis of the uncleaved APP molecules is mediated by the NPXY signal sequence in the cytoplasmic tail. The endocytosis of APP is the principal path for the generation of the 38-43 amino acid peptide that is subsequently secreted and deposited in the amyloid plaques. The binding of mDab1 PTB to APP may mediate the internalization of APP by effecting the membrane flow from the surface to intracellular membrane systems, and thereby affecting the generation of Aβ. Thus, the identification of agents that mediate mDab1 binding to APP may find use in influencing the way such peptides are produced, and mutations in mDab1 may be indicative of disease.

The distribution of mDab1 was determined by immunohistochemistry of hippocampal neurons, one of the cell types that are mislocalized in the mdab1 deficient mice. These neurons have a very characteristic morphology in culture with one dominant axonal trunk and several smaller dendritic off shoots. The majority of mDab1 and APP are seen in the cell soma. APP is known to be predominantly localized in the endosomal compartment. A small fraction was also detectable at the cell surface, but this population had a short half life. APP is sorted to the axons of neurons. Interestingly mDab1 is also enriched in axons. More mDab1 immunofluorescence was observed from the midzone region of the growth cone than from dendrites. In about 5 percent of neurons mDab1 was observed in the actin rich filapodia. mDab1 and APP have a similar distribution within hippocampal neurons.

The properties of mDab1 and genetic analysis of Dab in *Drosophila* suggest that these molecules function in key signal transduction pathways involved in the formation of neural networks.

In *Drosophila*, dab acts as a genetic enhancer of dAbl and is required for axonal pathfinding or fasciculation and acts together with Abl (Gertler et al., ibid. (1993) and Gertler et al., ibid. (1989)). However, it is not clear whether Dab and dAbl physically interact, whether Dab is regulated by tyrosine phosphorylation by dAbl nor whether Abl and Disabled are on the same or parallel pathways for axonal pathfinding. It is clear that redundant pathways exist (Elkins et al. *Cell* 60:565-575 (1990)). There are a number of parallels between axonal pathfinding and cell migration and mDab1-like molecules may be involved in both processes. No obvious pathfinding defects have been observed in the mdab1-1 mice. In the reeler mouse some malpositioned neurons connect successfully (Goffinet, *Anat. Embryol Berl.* 157:205-216 (1979)) but Reelin regulates neuronal connectivity in some systems (Del Rio et al. *Nature* 385:70-74 (1997)).

The requirement for Dab is unveiled under conditions where dAbl tyrosine kinase activity is absent. Thus, Dab must be functional under conditions where it is not tyrosine phosphorylated by dAbl. *Drosophila* Src (dsrc) may phosphorylate Dab under these conditions. Over-expression of kinase-defective dsrc during embryogenesis interferes with longitudinal connections in the CNS (Kussick et al., *Oncogene* 8:2791-2803 (1993)), reminiscent of dabl dab double mutants (Gertler, ibid. (1989)). The detection of mammalian mDab1, its ability to be phosphorylated on tyrosine and then bind SH2-containing PTKs, such as Src and Abl; and the binding of its PTB to tyrosine phosphorylated proteins in embryonic extracts, suggest that mDab1 might be regulated by PTKs during mammalian neurogenesis. Identification of mDab1 binding partners and a receptor for Reelin will help further elucidate the underlying mechanisms by which the activities of these gene products coordinate neuronal migration and axonal guidance.

During mammalian brain development, immature neurons migrate radially from the neuroectoderm to defined locations where they adopt distinct fates, giving rise to the characteristic layered brain (Hatten et al., *Curr. Opin. Neurobiol.* 3:38-44, (1993) and McConnell et al., *Neuron* 15:761-768 (1995)). During neuronal differentiation of P19 embryonal carcinoma cells, expression of mDab1 p60, p80 and p120 is induced, and the proteins are first tyrosine phosphorylated prior to neurite extension. Tyrosine phosphorylation of p80 correlates with axonogenesis becoming maximal at day 5 (E5). The expression pattern and phosphorylation of mDab1 are also regulated during mouse embryonic development. At embryonic day 10.5 (E10.5), mDab1 expression was detected only in developing nerves, but at E13 additional expression was observed in developing bone, possibly in precursors to osteoclasts. mDab1 p120 is expressed maximally at E9 and E10 and then declines, while mDab1 p80 persists in adults. Tyrosine phosphorylation of both these forms of mDab1 was observed in embryos but not in adults. mDab1 is therefore a substrate of a kinase that is active during neural development. The present invention further demonstrates that disruption of the mammalian disabled1 (mdab1) gene disturbs neuronal layering in the cerebral cortex, hippocampus and cerebellum. Thus mDab1 is required for correct positioning of neurons within the layered structures of the brain.

The mdab1 mutant phenotype closely resembles that of the reeler mouse (Goffinet et al., *Brain Res.* 318:263-276 (1984); Caviness et al., *J. Comp. Neruol.* 147:235-254 (1973); Stanfield and Cowan, *J. Comp. Neurol.* 185:393-422 (1979)), in which the secreted protein Reelin fails to be produced (D'Arcangelo et al., *Nature* 374:719-723 (1995); Ogawa et al., *Neuron* 14:899-912 (1995); Hirotsune et al., *Nat. Genet.* 10:77-83 (1995)). In both mdab1 and reeler mutant mice, neurons of a specific birthdate are found in an abnormal location. The Reelin protein, which has been proposed to act as extracellular signpost for migrating neurons, is localized normally in mice lacking mDab1 p80. Because mDab1 p80 is expressed in wild-type cortical neurons, the present invention indicates that it is part of a Reelin-regulated pathway that controls the final positioning of neurons.

mDab1 p80 is a docking protein with no known catalytic activity, so its function may be to link proteins together through its amino-terminal PI/PTB domain and tyrosine-phosphorylated motifs. This function may be regulated by extracellular signals. Thus, proteins that modify and bind to mDab1 p80, including non-receptor tyrosine kinases such as Src and Abl, may regulate neuronal migration. Mutations in non-redundant genes encoding other components of the signaling pathway might be expected to cause a mdab1-1-like phenotype. Mutations in src and abl do not affect brain development (Soriano et al., ibid. (1991); Schwartzberg et al. *Cell* 65:1165-1175 (1991); Tybulewicz et al., ibid. (1991)), but these tyrosine kinases may be redundant. An mdab1-1-like phenotype is seen with mutations in scrambler (Sweet et al., *Mamm. Genome* 7:798-802 (1996)), yotari (Yoneshima et al., *Neurosci. Res.* 29:217-223 (1997)), Cdk5 (Ohshima et al., *Proc. Natl. Acad. Sci. USA* 93:11173-11178 (1996)) and, p35 (Chae et al., ibid. (1997)). scrambler and yotari are mutations in mdab1 (Sheldon et al., *Nature* 389:730-733 (1997)). Cdk5 and p35 are the catalytic and regulatory subunits of a serine/threonine kinase that could potentially operate in a common signaling pathway with mDab1 p80 and Reelin. These molecules could also operate on mechanistically distinct processes that impinge on the laminar organization of neurons.

In another embodiment, the invention provides antibodies which bind to mDab1. The production of non-human antisera or monoclonal antibodies (e.g., murine, lagormorpha, porcine, equine) can be accomplished by, for example, immunizing an animal with mDab1 protein or peptides with or without an adjuvant. For the production of monoclonal antibodies, antibody producing cells are obtained from immunized animals, immortalized and screened, or screened first for the production of the antibody that binds to the mDab1 protein or peptides and then immortalized. It may be desirable to transfer the antigen binding regions (i.e., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397; which is incorporated by reference herein in its entirety.

Alternatively, a human monoclonal antibody or portions thereof may be identified by first screening a human B-cell cDNA library for DNA molecules that encode antibodies that specifically bind to mDab1 according to the method generally set forth by Huse et al. (*Science* 246: 1275-1281, 1989, which is incorporated by reference herein in its entirety). The DNA molecule may then be cloned and amplified to obtain sequences that encode the antibody (or binding domain) of the desired specificity.

It may be preferable to produce antibodies by genetic immunization using expression vectors to direct the expression of mDab1 proteins. Particle bombardment-mediated gene transfer (Tang et al., *Nature* 356: 152-154, 1992; Eisenbaum et al., *DNA & Cell Biol.* 12: 791-797, 1993; Johnston and Tang, *Meth. Cell Biol.* 43 Pt.A:353-365, 1994; Vahlsing et al., *J. Immun. Meth.* 175: 11-22, 1994) and retroviral gene transfer (Wang et al., *DNA & Cell Biol.* 12: 799-805, 1993; Stover, *Curr. Opin. Immunol.* 6: 568-571, 1994; and Laube et al., *Human Gene Ther.* 5: 853-862, 1994) have been used to generate specific antibody responses to proteins encoded by transferred genes. These methods permit the production of antibodies without requiring protein purification. Such methods may be used to produce panels of antibodies specific to native and mutant mDab1 proteins and muteins. Monoclonal antibodies may also be generated using these methods. These antibodies find use in purification methods and methods for screening for modulators of mDab1 activity or for detecting the presence of mDab1 in various diagnostic methods described herein or for detecting the presence of mutant forms of mDab1.

In further aspects of the invention, mDab1 proteins, peptides, fusion proteins and antibodies are used in a variety of screening and diagnostic methods. As will be evident to the common practitioner, the polynucleotide molecules, protein, peptides and antibodies of the present invention are useful in in vitro assays to screen for compounds capable of modulating the activity or expression of mDab1. Within these methods, the mdab1 genes and mDab1 proteins and peptides disclosed herein are useful for generating, isolating, and characterizing endogenous and exogenous factors, drugs and other agents that can be employed in methods to evaluate and/or regulate processes involved in normal and abnormal cell migration. The general methods of the invention provide methods directed toward the diagnosis and treatment of injury and disease conditions such as metastatic cancer, reactive gliosis, neurodegenerative diseases and Alzheimer's Disease. Within such assays, test compounds may be assessed for their ability to increase or decrease mDab1 activity or expression relative to a control assay in which the test compound is absent. Within another embodiment, test compounds are screened for the ability to modulate mDab1 activity by increasing or decreasing mDab1 expression.

In preferred diagnostic methods, labeled mDab1 proteins, peptides, or anti-mDab1 antibodies are employed to detect expression, localization and/or activity of mDab1 associated with normal and/or abnormal cells. In one general diagnostic example, mDab1 expression or activity is detected and/or quantified in a normal cell population or tissue, and these results are compared to expression or activity detected and/or quantified in a test cell population or tissue (for example a population of cancerous cells or cells from a site of neural injury). Detection and/or quantification of mDab1 expression, localization or activity can be accomplished by a variety of methods, such as by in situ hybridization using anti-mDab1 antibodies on embryos or tissue sections or within antibody microinjected cells, by Western blotting or immunoprecipitation using anti-mDab1 antibodies in cell or tissue lysates, or by affinity purification using anti-antibodies bound to a solid phase, among other methods. Comparable methods are disclosed herein, or are elsewhere disclosed and known in the art, for using non-antibody agents to detect and/or quantify mDab1 expression or activity.

Suitable non-antibody probes for use within these methods include, for example, oligonucleotide probes that hybridize to mDab1 transcripts, labeled binding partners of mDab1 such as Src, Fyn and Abl Sh2 domains, and synthetic or recombinant peptide analogs of mDab1 binding partners, among other useful probe types. For example, mdab1 cDNA and oligonucleotide probes may be useful in Northern, Southern, and dotblot assays for identifying and quantifying the level of expression of mDab1 in a cell. Measuring the level of mDab1 expression may provide prognostic markers for assessing the growth rate and invasiveness of tumors.

Differences that are detected and/or quantified between mDab1 expression or activity between normal and test cell populations or tissues may be diagnostic of particular disease states or other conditions characterized by aberrant cytoskeletal structure or regulation. In the case of cancerous or precancerous test cells, such as CML cells, a decrease of mDab1 expression compared to control cells is predictive of an increased risk of metastatic disease due to increased cell motility. In the case of test cells taken from sites of neural injury, the level of mDab1 expression or activity compared to control cells is predictive of the extent of neural regeneration that can be expected in a particular case, and may also be useful for determining preferred courses of treatment.

Additional diagnostic methods of the invention rely on labeled polynucleotide probes to map the chromosomal location of mDab1 to determine linkage of these genes relative to other genes and to identify genetic defects in these genes among cell populations or individuals.

The same steps and compositions that are employed within diagnostic methods of the invention are readily adapted for use within powerful screening methods provided by the invention. Screening methods that are particularly useful within the invention include high throughput screening assays designed to identify modulators of mDab1 expression or activity. In preferred screening assays, labeled mDab1 proteins, peptides, or anti-mDab1 antibodies are employed in a similar manner as described above to detect and/or quantify expression or activity of mDab1 in comparable test and control samples. Useful control samples in this context generally include a variety of in vivo or in vitro assay mixtures suitable for detecting and/or quantifying mDab1 binding to a selected binding partner, for example Abl. Useful test samples within these screening methods contain an added test substance, i.e., a putative mDab1 modulating agent, in qualitatively or quantitatively comparable assay mixtures to those of the control samples. In screens aimed at detecting modulators of mDab1 binding to a selected binding partner, the test sample contains suitable amounts of mDab1 protein and a selected binding partner under conditions that permit the formation of mDab1-binding partner complexes in the absence of the test substance. The complexes are then detected and/or quantified according the methods disclosed herein, and these results are compared to the results of detection and/or quantification of mDab1-binding partner complexes formed in the control sample.

Also provided are kits and multicontainer units comprising reagents and components for practicing the assay methods of the present invention. Kits of the present invention may, in addition to reagents for detecting mDab1, contain enzymatic reagents such as reverse transcriptase or polymerase; suitable buffers; nucleoside triphosphates; suitable labels for labeling the reagents for detecting mDab1 and developing reagents for detecting the signal from the label. In one aspect, kits of the present invention contain sequence-specific oligonucleotide primers for detecting polynucleotide molecules encoding mDab1. Such primers may be provided in a separate containers or may be provided in combinations of one or more primer pairs in a series of containers. One aspect of the invention provides kits containing mDab1 sequence-specific probes. Within yet another aspect, kits contain antibodies useful for detecting mDab1 (or mutants thereof) in a sample. Such kits contain mDab1-specific antibodies for detecting mDab1 protein. The mDab1-specific antibodies may be labeled or may be detected by binding to a secondary antibody. The antibody reagents may be provided in separate container or may be provided in combination in a series of containers. In addition to these components, the kits may also contain instructions for carrying out the assay and/or additional containers suitable for carrying out the reactions of the assay.

The following Examples are offered by way of illustration, not limitation.

EXAMPLE I

Identification of a Murine Homolog of Dab

Src interacting proteins involved in mouse embryonic development were identified using a modified yeast two-hybrid system as described by Vojtek et al. (*Cell* 74:205-214 (1993); which is incorporated by reference herein) and Hollenberg et al. (*Mol. Cell. Biol.* 15:3813-3822 (1995); which is incorporates by reference herein). A library of mouse embryo cDNAs (mixed embryonic day 9.5 and 10.5 (E9.5 and E10.5)) was prepared and inserted into the pVP16 expression vector (Vojtek et al., ibid. (1993) and Hollenberg et al., ibid. (1995)) to permit expression of VP16 transactivation domain fusion proteins. This cDNA library was screened for interaction with a fusion protein containing Src and the LexA DNA binding domain. To generate the Src-LexA fusion construct, the Src wild type cDNA was digested with BamHI and NsiI and ligated into the BamHI and PstI cloning sites of the pBTM116 vector (Vojtek et al., ibid. (1993) and Hollenberg et al., ibid. (1995)). The wild-type Src-lexA fusion construct was termed pBTM116-Src(wt).

The *Saccharomyces cerevisiae* strain L40 (Matα His3Δ200 trp1-900 leu2-3,112 ade2 LYS2::(lexAop)$_4$-HIS3 URA3::(lexAop)$_8$-lacZ GAL4) was transformed with the pBTM116-Src(wt) plasmid and the mouse embryo cDNA library described above. The Src-LexA fusion protein and the mouse embryo cDNA-VP16 fusion proteins alone are unable to activate transcription but stable interaction between them results in the transcription of the yeast HIS3 gene and the bacterial lacZ gene (Vojtek et al., ibid. (1993); Hollenberg et al., ibid. (1995); Vojtek & Hollenberg, *Meth. Enzymol.* 255:331-342 (1995)). Transformants were grown on minimal media lacking tryptophan, leucine and histidine for two days, and colonies were picked and analyzed for β-galactosidase expression by a filter lift assay.

Yeast transformants that expressed levels of β-galactosidase detectable within 3 hours were grown in media containing tryptophan and characterized for the loss of the pBTM116-Src(wt) plasmid. Individual library isolates were placed into groups based on β-galactosidase production in the progeny of the crosses with L40 strain containing the library isolate and the AMR70 strain (Matα his3 lys2 trp1 leu2 URA3:(lexAop)$_8$-lacZ Gal4) expressing different LexA fusion proteins. These LexA fusions proteins included LexA-lamin (Vojtek et al., ibid. (1993); Hollenberg et al., ibid. (1995)), LexA-Src(wt), LexA-Src(FF), LexA-Src (ΔSH3), LexA-Src(SH2') and LexA-Src(295R). These mutants were prepared as described. The Src mutant Src(FF) contained Phe residues in place of Tyr 416 and Tyr 526 was prepared as described by Cooper and MacAuley (*Proc. Natl. Acad. Sci. USA* 85: 4232-4236 (1988); which is incorporated by reference herein); Src(ΔSH3), a SH3 deletion mutant, was prepared as described by MacAuley and Cooper (*Mol. Cell. Biol.* 8:3560-3564 (1988); which is incorporated by reference herein); and Src(295R), a kinase-inactivated Src was prepared as described by Seidel-Dugan et al. (*Mol. Cell. Biol.* 12:1835-1845 (1992); which is incorporated by reference herein). The Src(SH2') mutation was generated by PCR and changed the critical Arg 175 in the phosphate binding pocket to Lys, the adjacent Glu 175 was changed to Ser and a unique SalI site was introduced. The mutation was confirmed by restriction and sequence analyses. This mutation was predicted to reduce binding to tyrosine phosphorylated peptides since Arg 175 makes contact with the phosphate of bound peptides (Waksman et al., *Nature* 358:646-653 (1992)) and the equivalent substitutions in the Abl SH2 domain abolished binding (Mayer et al, *Mol. Cell. Biol.* 12: 609-618 (1992)). Of $5\times10^6$ clones analyzed, 200 scored positive for both reporters with wild-type Src and 70% of these were dependent upon the catalytic activity of Src.

Total DNA was purified from selected library isolates, transformed into the XL-1 BLUE bacterial strain (Stratagene Cloning Systems, La Jolla, Calif.). DNA was sequenced with a primer that hybridizes to the pVP16 vector 5'-GCAA-GATCTTAGGGATCGATTGG-3' (SEQ ID NO:1) and an M13 universal primer. Sequence comparisons were carried out using the Genetics Computer Group (GCG) programs and compared against the GenBank, SwissProt, and PirProtein databases using the FASTA program (Pearson & Lipman, *Proc. Natl. Acad. Sci. USA* 93:2444-2448 (1988)). Two known Src interacting proteins, Fak (Cobb et al., *Mol. Cell. Biol.* 14:147-155 (1994) and Schaller et al., *Mol. Cell. Biol.* 14:1680-1688 (1994)), and Sam68 (Taylor & Shalloway, *Nature* 368:867-871 (1994) and Fumagalli et al., *Nature* 368:871-874 (1994)) were identified in addition to a number of cDNAs encoding novel proteins. Two identical cDNA clones, designated B3 and C46, had significant homology with the *Drosophila* dab gene and were analyzed further.

EXAMPLE II

Identification and Analysis of mDAB1 cDNA

Complete cDNA clones for mDab1 were isolated by screening embryonic mouse libraries using the cDNA clone B3 as a probe (corresponding to nucleotides 579 to 1091 of SEQ ID NO:2) according to standard techniques (Sambrook et al., *Molecular Cloning*, 2nd ed., vol. 1-3, Cold Spring Harbor Laboratory Press, Cold Spring Harbor (1989); which is incorporated herein by reference). Three clones, designated mDab555, mDab271 and mDab217, were identified. The mDab555 and mDab271 full length cDNAs were obtained from a pCDNAI (Invitrogen, Carlsbad, Calif.) library of E15-17 mouse brain cDNAs (obtained from Visha Dixit, University of Michigan, Ann Arbor, Mich.) and mDab217 was from a λYES (Stratagene Cloning Systems) library made with embryonic stem cell cDNAs (from Zhi Chen, University of Michigan, Ann Arbor, Mich.).

Each cDNA was subcloned into pBLUESCRIPT (Stratagene Cloning Systems). Nested deletion mutants were generated with sequential exonuclease III and S1 nuclease treatments at 37° C. (Sambrook et al., ibid. (1989)). Automated DNA sequencing was performed with plasmid templates on a BIOSEQUENCER (The Perkin-Elmer, Corp.— PE Applied Biosystems Division, Foster City, Calif.), and overlapping sequences for each clone were obtained for both strands.

The three clones represented at least three different mRNAs, encoding mDab1 isoforms of 555, 217 and 271 residues. The nucleotide sequences and predicted amino acid sequences of the three clones mDab555, mDab217 and mDab271 are shown in SEQ ID NO:2 and SEQ ID NO:3; SEQ ID NO:4 and SEQ ID NO:5; and SEQ ID NO:6 and SEQ ID NO:7, respectively. A comparison of the sequences shows that the mDab217 mRNA diverges from mDab555 at a consensus splice donor sequence at codon 199, encodes a further 18 residues before a termination codon, and terminates with a 3' untranslated sequence distinct from mDab555. The mDab271 mRNA contains an additional exon of 270 nucleotides inserted between codons 241 and 242 of mDab555. This exon encodes 30 residues before a stop codon. A fragment of a potential fourth cDNA was identified using RT PCR, and contained an insert in the mDab555 mRNA at another consensus splice donor sequence between residues 239 and 242. The nucleotide sequence and deduced amino acid sequence of the exon are shown in SEQ ID NO:8 and SEQ ID NO:9.

The B3 and C46 clones isolated in the two-hybrid screen include residues 106 to 274 of mDab555 (SEQ ID NO:3). The common mDab1 initiation codon is preceded by an in-frame termination codon and is in a good consensus for translational initiation (Kozak, *J. Biol. Chem.* 266:19867-19870 (1991)).

The chromosomal location of the mdab1 gene was mapped using Southern blotting to follow polymorphic restriction fragments, in the progeny of the backcross (C57BL/6J X *Mus* spretus)F1 X C57BL/6J, and the reciprocal backcross. mdab1 was localized to mouse chromosome 4, at offset 70.6. This portion of the mouse chromosome is syntenic with the human chromosome 1p32-31 region.

A database search using the mDab1 sequences identified several mDab1 relatives including p96 (Xu et al., *J. Biol. Chem.* 270:14184-14191 (1995), now referred to as mDab2; Genbank accession U18869) and its human homolog, DOC2 (Mok et al., *Gyn. Oncol.* 52:247-252 (1994); Albertsen et al., *Genomics* 33:207-213 (1996), *Genbank Accession No.* U39050), that are widely expressed proteins. A mDab-related gene, M110.5, was also identified in the *C. elegans* genome sequencing project (Wilson et al., *Nature* 368:32-38 (1994)). Alignments of the PTB domains of these proteins with the mDab PTB domain were calculated with GCG Pileup and similar amino acids were boxed with EGCG Prettyplot (threshold 0.8, plurality 3).

An alignment of these proteins with mDab1 and *Drosophila* Dab shows greatest sequence conservation in an amino-terminal region of 136 residues contained within the amino acid sequence from residue 27 to 170 of SEQ ID NO:3 (Howell et al., ibid. (1997); which is incorporated by reference herein). Through this region Dab and mDab1 are 52% identical (72% similar). The mDab1 and the *Drosophila* Dab proteins are related in two other areas. One stretch of 73 amino acids from residue 400 in mDab555 and 1913 in *Drosophila* Dab, is 20.5% identical (41% similar) and has an unusually high concentration of hydroxy-amino acids (19%), glutamine (12%), and proline (12%). Another stretch of 33 amino acids, from residue 508 in mDab555 and 2082 in Dab, is 36% identical (45% similar) and also rich in hydroxy amino acids (19%). The two similar hydroxy amino acid rich regions may represent conserved sites of phosphorylation. The *Drosophila* Dab protein is known to be phosphorylated to high stoichiometry on serine (Gertler, ibid. (1992)), which may be important for its function.

Bork & Margolis (*Cell* 80:693-694 (1995)) pointed out that the amino-terminal conserved region of Dab is distantly related in sequence to the ShcA PTB domain (also known as PI domain) (Kavanaugh & Williams, *Science* 266:1862-1865 (1994)). The ShcA PTB is composed of a β sandwich that is capped with a charged α helix (Zhou et al., *Nature* 378:584-592 (1995)), and the phosphopeptide ligand fits into a groove between them. The N-terminal part of the phosphopeptide extends as a beta strand that fits the groove and extends the beta sheet of the PTB domain, making the side chains and backbone contacts with the PTB domain. A specific phosphopeptide binds antiparallel to the β5 strand of the PTB and is stabilized by contacts with several residues in the PTB. The phosphotyrosine on the peptide interacts with several hydrophilic and positively-charged residues at one end of the PTB, including Arg 67, Ser 151, Lys 169, and Arg 175. These residues are conserved across the Shc group of PTBs (Kavanaugh & Williams, ibid. (1994); Lai et al., *Mol. Cell. Biol.* 15:4810-4818 (1995); O'Bryan et al., *Proc. Natl. Acad. Sci. USA* 93:2729-2734 (1996)). Mutation of Arg 67 or Arg 175 to Gln reduced binding of the ShcA PTB to phosphorylated targets by 36% and 100%, respectively (Zhou et al., ibid. (1995)). The residues amino-terminal to the phosphorylated tyrosine in the phosphopeptide bound to the ShcA PTB include the Asn Pro Xaa pTyr (NPXpY) consensus sequence (Batzer et al., *Mol. Cell. Biol.* 15:4403-4409 (1995); Kavanaugh et al., *Science* 268:1177-1179 (1995); Songyang et al., *J. Biol. Chem.* 270:14863-14866 (1995); van der Geer et al., *Curr. Biol.* 5:404-412 (1995)). These residues contact the β sheet and α3.

Alignment of the mDab1 and ShcA PTBs was facilitated by the solution structure of the ShcA PTB (Zhou et al., ibid. (1995)) and secondary structure predictions for mDab1 and the dnumb PTB (Zhou et al., ibid. (1995)), which represents a phylogenetic intermediate between the Shc and Dab family PTBs. mDab1 has residues that correspond with critical amino acids in the ShcA PTB that contact the phosphate moiety, including Arg 67, Ser 151 and Lys 169. However, the region between ShcA β1' and β2' is quite divergent in mDab1, and there is no apparent homolog of Arg 175 of ShcA. The PTB of IRS-1 is also divergent in this region (Eck et al, *Cell* 85:695-705 (1996); Zhou et al., *Nature Struct. Biol.* 3:388-393 (1996)). Some of the residues that contact the peptide ligand amino-terminal to the phosphotyrosine are conserved. In particular, Phe 198 in β3 of ShcA is conserved in Dab family members and dNumb. This residue contacts the side chain of Asn −3 of the ligand. These sequence similarities suggest that the amino-terminal region of mDab1 may adopt a similar fold to the ShcA PTB and may function to bind to phosphorylated proteins or peptides.

EXAMPLE III

Preparation of GST Fusion Protein and Antibodies

Two GST fusion constructs were made with the mDab555 cDNA to facilitate the preparation antibodies. Both were cloned between the BamHI and EcoRI sites in the glutathione S-transferase gene fusion vector, pGEX-2T (Amersham Pharmacia Biotech, Inc., Piscataway, N.J.) polylinker. The first construct corresponds to the region cloned in the yeast two-hybrid screen comprised of residues 107 to 243, that was PCR amplified with the oligonucleotide pairs 5'CGCGGATCCCATCACCATGCTGTTCATGAA-3'(SEQ ID NO:10) and 5'-CGCGAATTCCGACGG GAGAAAGGCATCAC-3' (SEQ ID NO:11). The second fusion protein contains the region corresponding to the mDab1 PTB, residues 29 to 197, that was PCR amplified with the oligonucleotides 5'-CGCGGATCCGC-CACTTTGATAAAGAGGT-3, (SEQ ID NO:12) and 5'-CCGGAATTCCACGGGATCTTCCACATC-3'(SEQ ID NO:13). The GST fusion constructs were transformed into *Escherichia coli* strain TG-1.

The GST fusion proteins were affinity purified from lysates of TG-1 by adsorption onto glutathione-agarose resin (Amersham Pharmacia Biotech), followed by 4 washes with lysis buffer (phosphate buffered saline, 1% TRITON X-100 (t-octylphenoxypolyethoxyethanol), 20 μg per ml aprotinin, and 1 mM PMSF (phenylmethylsulfonyl fluoride)). The fusion constructs were either used directly as affinity matrices or eluted with 5 mM reduced glutathione as previously described (Okada et al., ibid. (1993)). The GST-fusion protein concentrations were determined by comparison to known amounts of protein on Coommasie blue stained SDS-polyacrylamide gels.

Rabbit polyclonal antibodies against mDab1 were prepared by immunizing New Zealand White female rabbits with a GST-mDab1 fusion corresponding to residues 107 to 243 (B3) or with peptide N (Cys Glu Leu Gln Val Ala Ala Ala Val Lys Thr Ser Ala Lys Lys Asp Ser Arg Lys Lys) (SEQ ID NO:14) and peptide C (Cys Gly Glu Pro Pro Ser Gly Gly Asp Asn Ile Ser Pro Gln Asp Gly Ser) (SEQ ID NO:15) that correspond to the mDab555 sequence beginning at residues 6 and 542 respectively. All sera were affinity purified with the corresponding antigen immobilized on cyanogen bromide activated SEPHAROSE (beaded agarose) (Sigma, St. Louis, Mo.) or SULFOLINK (immobilized iodoacetyl on a crosslinked agarose support) (Pierce Chemical Company, Rockford, Ill.). Resulting affinity-purified antisera were designated anti-mDab(B3), anti-mDab(N) and anti-mDab(C) reflecting the immunogen used to generate the antisera.

The Src polyclonal sera 3060 was raised to a peptide corresponding to residues 519 to 533 of c-Src (Cooper et al., *Science* 231:1431-1434 (1986)). The anti-phosphotyrosine monoclonal 4G10 was obtained from Deborah Morrison (National Cancer Institute, Frederick, Md.) (Druker et al., *New Eng. J. Med.* 321:1383-1391 (1989)).

EXAMPLE IV

Expression of mDab1 a. Analysis of mDab1 mRNA Expression

Northern analysis was carried out on a blot provided by Anne Vojtek (University of Michigan Medical Center, Ann Arbor, Mich.) which contained adult mouse total RNA from brain, heart, kidney, liver, SK muscle, spleen and uterus tissue; total RNA from 10T1/2 mouse fibroblasts and mouse embryo E10.5 RNA. The mDab1 B3 cDNA probe was radioactively labeled with [α-$^{32}$P]dCTP using the random-prime DNA labeling kit (United States Biochemical, Cleveland, Ohio) according to the manufacturer's instructions. The blot was prepared as described (Vojtek & Cooper, *J. Cell Sci.* 105:777-785 (1993)), probed with the heat-denatured radioactively-labeled B3 cDNA probe, and incubated under standard hybridization conditions (Sambrook et al., ibid. (1989)).

Northern analysis of the adult mouse tissues showed that mDab1 expression was largely restricted to brain. Expression was also high in E10.5 (10.5 days post coitus) embryos. Three transcripts of 5.5, 4.0 and 1.8 kb were detected. The 1.8 kb mRNA probably encodes the mDab1 217 isoform. The 5.5 and 4.0 transcripts are larger than the largest cDNA identified herein suggesting that mDab1 has an extensive 5' untranslated region or that additional spliced forms exist.

b. Expression and tyrosine phosphorylation of mDab1 in Cultured Cells.

In a survey of cultured cells, mDab1 expression was found to be limited to differentiated P19 embryonal carcinoma cell cultures and various hematopoietic cell lines. mDab1 expression was not detected in the neuroblastoma- or neural crest-derived lines SY5Y and PC12, or in the fibroblast lines Rat1, 10T1/2 or NIH3T3. P19 cells are pluripotent and can be induced to differentiate into neural ectoderm when grown in aggregates in the presence of all-trans-retinoic acid (RA) (McBurney et al., *Nature* 299: 165-167 (1982); Jones-Villeneuve et al., *Mol. Cell. Biol.* 3:2271-2279 (1983)). Three to 5 days after addition of RA, P19 cultures are composed of glioblasts and neuroblasts. By 7 days, greater than 50% of the cells are axon-bearing embryonic neurons, and the remainder are glia (Rudnicki & McBurney, ibid. (1987)).

Expression and tyrosine phosphorylation of the mDab1 isoforms during P19 cell differentiation and neural development were determined by inducing P19 EC cells to differentiate along the neural lineage by treatment with RA at specific intervals and immunprecipitating cell lysates with either anti-mDab(B3) or preimmune antibodies. P19 EC cells (obtained from John C. Bell and Ninan Abraham, University of Ottawa, Ottawa, Ontario, Canada) were grown and induced to differentiate as described by Rudnicki & McBurney (*Teratocarcinomas and Embryonic Stem Cells: A Practical Approach*, IRL Press Limited, Oxford, England, pages 19-47, (1987); which is incorporated herein by reference).

Cell lysates were prepared by lysing $1 \times 10^6$ cells on ice in 1 ml of TX-IPB (0.1 M NaCl, 1% TRITON X-100, 10 mM HEPES (N-2-hydroxyethyl-piperazine-N'-2-ethanesulfonic acid) pH 7.4, 2 mM EDTA, 0.1% 2-mercaptoethanol, 20 µg of aprotinin per ml, 50 mM NaF, 0.2 mM NaOH, 2 mM PMSF, 1 mM phenylarsine oxide) for 10 minutes on ice. The lysates were clarified by centrifuging at 20,000×g for 30 minutes and cleared with SEPHAROSE CL-4B (cross-linked beaded agarose at a concentration of approximately 6% agarose) (Sigma). The protein concentration was adjusted to 3 mg of protein per ml unless otherwise stated.

Cell lysates were immunoprecipitated with anti-mDab (B3) or preimmune antibodies, which were prebound and chemically crosslinked to protein SEPHAROSE beads by treatment with dimethyl pimelimidate (Schneider et al., *J. Biol. Chem.* 257:10766-10769 (1982); which is incorporated by reference herein). The bound antibodies were mixed with the lysates for 90 minutes at 4° C., followed by 4 washes with TX-IPB buffer.

The proteins were eluted by addition of two-times concentrated gel loading buffer (4% sodium dodecyl sulfate (SDS), 40% glycerol, 0.2M Tris-HCl (pH 6.8), 5.6 M 2-mercaptoethanol, 5 mM EDTA, 0.02% bromophenol blue). The samples were boiled for 10 minutes prior to analysis by SDS polyacrylamide electrophoresis (SDS PAGE). The immunoprecipitates were electrophoresed by SDS PAGE and were immunoblotted to detect mDab1 with anti-mDab(B3) antibody and phosphotyrosine with 4G10 antibody. Immunoblotting was performed as described by Howell & Cooper (ibid. (1994); which is incorporated by reference herein). Immunoreactive proteins were visualized by enhanced chemiluminescence (ECL) detection system (Amersham Pharmacia Biotech Inc.).

Differentiated P19 cultures were found to express the 60, 80 and 120 kDa mDab1 isoforms by immunoblot analysis of anti-mDab1 immunoprecipitations from lysates of these cells. However, in undifferentiated P19 cells, only p80 was observed. The abundance of this isoform increased about 5 fold during neuronal differentiation, then declined after day 5. The p60 and p120 isoforms were not detected in undifferentiated cells, and their expression peaked at day 3 of differentiation.

Immunolot analysis of the same immunoprecipitates with anti-phosphotyrosine antibodies revealed that the p60, p80 and p120 were tyrosine phosphorylated during differentiation, with the maximal phosphorylation of all proteins occurring at day 5. No change in mDab1 expression or tyrosine phosphorylation was detected when P19 cells were induced to differentiate into muscle lineages (Edwards et al., *Mol. Cell. Biol.* 3:2280-2286 (1983)). Various isoforms were detected in the hematopoietic cell lines LSTRA (120, 36 kDa), Jurkat (120, 36 kDa), K562 (36 kDa), and 32D (120, 45 kDa).

Using anti-peptide antibodies, it was found that the p80 and p60 forms of mDab1 contain the common amino-terminal sequence encoded by all of the cloned cDNAs, and that the p120 and p80 forms contain the C-terminal sequence specific to the mDab555 mRNA. In vitro translated mDab555 has an apparent molecular mass of 75 kDa. When expressed in fibroblasts, mDab555 migrates at 80 kDa, possibly due to phosphorylation, and comigrates with p80 detected in P19 cells. The p45 and p36 forms detected in hematopoietic cells react with the anti-mDab(B3) and anti-mDab(N) antibodies, and appear to correspond to the products of the mDab271 and mDab217 mRNAs, respectively. The mRNAs encoding the p60 and p120 forms have not yet been cloned, but it was assumed that these proteins contain the PTB, since they react with anti-mDab(B3) antibody.

c. Expression and tyrosine phosphorylation of mDab1 During Embryogenesis

To determine the expression pattern of mDab1 during mouse embryogenesis, extracts from the heads and trunks of mouse embryo were prepared at E9, E10, E11, E12, E13 stages of development. The lysates were immunoprecipitated with anti-mDab(B3) or preimmune sera followed by immunoblotting with anti-mDab or anti-phosphotyrosine antibodies essentially as described above.

Immunoprecipitation and Western blotting procedures detected both mDab1 p80 and p120 in lysates from heads of embryonic mice, whereas expression in the trunk lysates was much lower. mDab1 p120 was detected at E9, which corresponds to early stages of neural development (Stainier & Gilbert, *Proc. Natl. Acad. Sci. USA* 87:923-927 (1990)) and at E10. The expression of p120 decreased after E10 and was not detected in adult brain. In contrast, the expression of mDab1 p80 increased between E10 and E11 and remained high in adult brain. The tyrosine phosphorylation of mDab1 p80 was maximal at E10 and E11, declining thereafter and becoming undetectable in the adult brain.

d. Identification of Kinases that Phosphorylate mDab1 mDab1 tyrosine phosphorylation was examined at E13 in mice homozygous for mutations in the src, fyn or abl genes (Soriano et al., *Cell* 64:693-702 (1991); Tybulewicz et al., (*Cell* 65:1153-1163 1991); Stein et al., *Cell* 70:741-750 (1992)) to determine whether the Src, Fyn or Abl kinases phosphorylate mDab1 during mouse brain development. mDab1 was immunoprecipitated from lysates of mutant E13 embryos and wild-type E13 embryo littermates. Phosphotyrosine levels in the lysates were determined by Western blotting as generally described above to assess both mDab1 expression and phosphorylation levels. The levels of mDab1 isoforms and their levels of phosphorylation were the same in mutant and wild-type animals suggesting that none of the kinases alone was responsible for mDab1 phosphorylation. mDab1 is therefore phosphorylated either by a number of redundant kinases or by a yet untested kinase.

e. Localization of mDab1 Expression in Embryonic Cell Types

To establish which cell types were expressing mDab1, mDab1 was localized by whole mount immunodetection in E10.5 embryos. Mouse embryos (day E10.5) were incubated in wholemount with anti-axonal antibodies (mouse monoclonal 2H3) or anti-mDab(B3) antibodies. Embryos were fixed and permeabilized as described (Hogan et al., *Manipulating the Mouse Embryo, A Laboratory Manual,* 2nd ed., Cold Spring Harbor Laboratory Press, Cold Spring Harbor, N.Y., pages 325-384 (1994); which is incorporated by reference herein). Subsequent incubations were for 12 hours each at 22° C. in 2% instant skim milk in PBS. Immunodetection of mDab1 was accomplished with anti-mDab(B3) antibody and sequential additions of goat anti-rabbit antisera (Jackson ImmunoResearch Laboratories, West Grove, Pa.), followed by FITC conjugated donkey anti-goat antisera (Jackson ImmunoResearch Laboratories). Axons were detected using the monoclonal 2H3 (Placzek et al., *Devel.* 110:19-30 (1990)) (obtained from Thomas Jessell, Columbia University, New York) and subsequent incubations with sheep anti-mouse antisera, and Texas red conjugated donkey anti-sheep antisera (Jackson ImmunoResearch Laboratories, West Grove, Pa.).

Indirect fluorescence indicating antibody binding was detected with a DELTAVISION microscope (Applied Precision Inc., Issaquah, Wash.). Fluorescence patterns observed when anti-mDab(B3) and anti-2H3 antibodies were incubated individually were identical to results obtained when used together. All secondary, tertiary, antibody alone, and mDab1 preimmune controls were negative. Nerve tracts were identified by double label immunostaining with antibody to a general axonal marker as described by Placzek et al. (ibid. (1990)). mDab1 expression was observed in the head in neural tracts corresponding to the developing cranial nerves, such as the oculomotor and the trochlear nerves. In the body, mDab1 expression in the spinal accessory nerve and dorsal root ganglia was apparent. At day E13, mDab1 expression was observed in sensory nerves that innervate the vibrissae, and in developing bone in the extremities. All nerves identified at these times by neurofilament antibody also expressed mDab.

These results demonstrate that mDab1 is localized in nerves and is tyrosine phosphorylated at times when the nervous system is undergoing rapid expansion and axonal networks are developing. mDab1 is expressed in the adult brain, but is not detectably tyrosine phosphorylated suggesting that mDab1 interacts with protein-tyrosine kinases during the development of the nervous system and may act to transduce signals during development.

f. Interaction of mDab1 with Src

The identification of mDab1 in a yeast two-hybrid screen using Src as the bait suggested that mDab1 would interact with phosphotyrosine kinases (PTKs). To determine the nature of the interaction between mDab1 and Src, β-galactosidase expression in yeast expressing mDab1 clone B3 and various Src mutant-LexA fusions including Src(FF), Src(ΔSH3), Src(295R) and Src(SH2').

The Src wild type cDNA and each mutant were amplified by polymerase chain reaction (PCR) amplification using the primers (5'-CTCGGATCCTCATGGGGAGCAGCAA-GAGCA-3') (SEQ ID NO:16) and (5'-CTCATGCATC-CTATAGGTTCTCTCCAGG-3') (SEQ ID NO:17), directed to the amino- and carboxyl-terminus of Src, respectively. Each PCR product was digested with BamHI and NsiI and ligated into the BamHI and PstI cloning sites of the pBTM116 vector (Vojtek et al., ibid. (1993) and Hollenberg et al., ibid. (1995)) to generate the Src-LexA fusion constructs. Pairs of Src-LexA and mDab1-VP16 fusion proteins were coexpressed in *Saccharomyces cereviseae* strain L40 as described previously. β-galactosidase activity was detected by filter assay. The Src mutants Src(ΔSH3) and Src(FF) interacted with mDab1 as strongly as did wild-type Src. However, neither the Src(SH2') nor the Src(295R) mutants interacted with mDab1. The Src-mDab1 interaction therefore requires tyrosine phosphorylation of mDab1 but not Src and requires the SH2 domain and not the SH3 domain. This is consistent with the model that phosphorylation of mDab1 in the region encoded by the cDNA clone B3 provides a binding site for the SH2 domain of Src.

EXAMPLE V

Interaction of mDab1 and Src and Other Phosphotyrosine Kinases in Mammalian Cells a. Interaction of mDab1 with Src To test whether the mD ab555 product, p80, was phosphorylated by Src in mammalian cells, mDab555 (p80) was expressed alone or together with activated Src (Src527F) in 293T fibroblasts. For expression in mammalian cells the entire open reading frame of the mDab555 cDNA was PCR amplified with the oligonucleotides 5'-CGCGGATCCAG-GATGTCAACTGAGACA-3' (SEQ ID NO:18) and 5'-CGCGGATCCTTCACTGGGCGACTGTGAGT-3' (SEQ ID NO:19) and ligated into the BamHI site of the pLXSH retroviral vector (Miller et al., *Meth. Enzmmol.* 217:581-599 (1993)). The retroviral vector pLXSHD-Src(527F) (Howell & Cooper, *Mol. Cell. Biol.* 14:3813-3822 (1994); which is incorporated by reference herein) contained the activated Src527F cDNA in the pLXSH retroviral vector.

Virus was produced (Afar et al., *Science* 264:424-426 (1994)) by cotransfecting the retroviral DNAs with a ecotrophic packaging vector containing gag, pol and env genes obtained from Owen Witte (University of California, Los Angeles, Calif.) into 293T cells (obtained from Robert Eisenman, Fred Hutchinson Cancer Research Center, Seattle, Wash.). Virus, which was collected 60 hours post infection, was mixed with 4 μg/mL; Sigma, St. Louis, Mo.) POLYBRENE (hexadimethrine bromide) Sigma, St. Louis, Mo.) and filtered through 0.45 μm filters prior to addition to target cells. Cells were selected in hygromycin (50 μg/mL; Calbiochem-Novabiochem Corp., San Diego, Calif.) or L-histidinol (2 mM; Sigma, St. Louis, Mo.) starting 24 hours after addition of virus.

mDab1 was recovered by immunoprecipitation from cell lysates with mDab1 or preimmune antibodies essentially as described previously. Immunoprecipitations were subjected to SDS PAGE as described above and immunoblotted with either anti-mDab1 or anti-phosphotyrosine to assess mDab1 expression and phosphotyrosine content. Expression of Src527F induced the tyrosine phosphorylation of mDab1 p80, suggesting that mDab1 p80 is a substrate for Src or a Src-activated tyrosine kinase.

b. Interaction of mDab1 with Phosphotyrosine Kinase SH2 Domains

To determine whether the phosphorylation of mDab1 generates binding sites for the SH2 domain of Src or other PTKs, phosphorylated and unphosphorylated mDab1 p80 were tested for binding to SH2 domains of other phosphotyrosine kinases. The GST-Src(SH2), GST-Fyn(SH2), GST-Abl(SH2) (obtained from Joan Brugge (Harvard, Boston, Mass.) and Jean Y. Wang (University of California at San Diego, San Diego, Calif.) and GST-CSK(SH2) constructs were described by Okada et al. (*J. Biol. Chem.* 26B:18070-18075 (1993)) and Duyster et al. (*Proc. Natl. Acad. Sci. USA* 92:1555-1559 (1995)) were used to assess p80 binding.

Lysates from 293T cells transfected with retroviral vectors encoding mDab555 alone; Src 527F alone; Src527F and mDab555 together; or Src527F and mDab1 98/200F, which is described in more detail below, were either bound to immobilized GST fusions proteins or were immunoprecipitated with anti-mDab1 or preimmune antibodies. Binding assays and analysis were carried out essentially as described for immunoprecipitations with 5 µg of GST fusion protein immobilized on glutathione agarose beads. Phenyl phosphate and phosphoserine were used at 50 mM for competition experiments. After washing, mDab1 bound to the immobilized SH2 domains was detected by immunoblotting. Tyrosine phosphorylated but not control mDab1 associated with the Src, and Fyn SH2 domains in vitro. mDab1 also interacted with the Abl SH2 domain, but less well than with Src or Fyn, and did not interact with the Csk SH2 domain. The Abl and Csk SH2 domains do form high affinity complexes with other tyrosine phosphorylated molecules however (Sabe et al., *Proc. Natl. Acad. Sci. USA* 91:3984-3988 (1994); Duyster et al., ibid. (1995)).

c. Overexpression of mDab1 and Src527F in Mammalian Cells

To examine whether mDab1 and Src527F would form complexes in mammalian cells, both proteins were overexpressed in Rat-1 fibroblasts (obtained from Robert Eisenman, Fred Hutchinson Cancer Research Center, Seattle, Wash.). Cell lysates were immunoprecipitated with either anti-Src antibodies or preimmune serum, and mDab1 was detected by immunoblotting with anti-mDab1 antibody essentially as described above. mDab1 co-immunoprecipitated with Src, and was detected with both anti-mDab1 antibodies and antiphosphotyrosine antibodies. Approximately 1% of the phosphorylated mDab1 that was present in the total cell lysate was immunoprecipitated. In addition Src was detected in anti-mDab immunoprecipitates. A 60 kDa tyrosine-phosphorylated protein detected in mDab1 immunoprecipitates from 293T cells expressing mDab1 and Src527F was confirmed to be Src. These results demonstrated that Src and mDab1 p80 formed complexes stable enough to be isolated from cells in the presence of non-ionic detergent.

d. Identification of Tyrosine Residues Involved in Src SH2 Binding

Examination of the protein sequences of mDab1 revealed no consensus Src SH2 (Songyang et al., *Cell* 72:767-778 (1993)) or SH3 (Feng et al., *Science* 266:1241-1247 (1994); Yu et al., *Cell* 76:933-945 (1994); Mayer & Eck, *Curr. Biol.* 5:364-367 (1995)) binding sites. mDab1 p80 and p45 contain two sequences Val Tyr Gln Xaa Ile (SEQ ID NO:20) (Tyr 185 and Tyr 198) which may represent Src or Fyn binding sites. These regions, including the B3 region contains a motif Tyr Gln Tyr Ile (SEQ ID NO:21), is similar to the Src binding site, Tyr Ile Tyr Val (SEQ ID NO:22) on the PDGF receptor (Mori et al., *EMBO J.* 12:2257-2264 (1993); Alonso et al., *J. Biol. Chem.* 270:9840-9848 (1995)). The first tyrosine in this motif, Tyr 198, is a likely site to be tyrosine phosphorylated by the Src family kinases (Songyang et al., *Nature* 373:536-539 (1995)). Two sequences Ile/Val Tyr Gln/Asp Val Pro (Tyr 220 and Tyr 232) that may represent binding sites for Abl and/or Crk (Songang et al., ibid. (1993)).

To test the effect of mutations at the Tyr 198 and Tyr 200 residues on binding sites for the Src SH2 domain, a mutant mDab555 was generated which contained Phe residues in place of both Tyr 198 and Tyr 200. The mutant mDab555 was generated by oligonucleotide site-directed mutagenesis as described previously (Kunkel et al., *Meth. Enzymol.* 154:367-382 (1987); which is incorporated herein by reference), with the oligonucleotide 5'-CACAATGAACTG-GAAGACGGGATCTTCCAC-3'(SEQ ID NO:23). This mutagenesis simultaneously introduced both mutations and was designated mDab198/200F. Mutants were identified by screening colonies for the introduction of a unique BbsI site into the mDab555 cDNA and were confirmed by sequence analysis. The mutant cDNA was inserted into the retroviral vector as described above to analyze the effect of these mutations on binding sites for the SH2 domain of Src or other PTKs. Lysates from 293T cells transfected with retroviral vectors encoding mDab555 alone; Src 527F alone; or Src527F mDab198/200F were either bound to immobilized GST fusions proteins with the Src, Csk, Fyn or Abl SH2 domain or were immunoprecipitated with anti-mDab1 or preimmune antibodies essentially as described above. After washing, mDab1 bound to the immobilized SH2 domains was detected by immunoblotting. The in vivo association between mDab1 and Src was reduced about 2-fold by the mutation. These results suggest that Tyr 198, or Tyr 200 and another of the six tyrosines in the B3 region of mDab1 may be Src binding sites.

e. The Association between Src and mDab1 in Differentiating P19 Cells

To determine whether the interaction between mDab1 and Src could be detected under conditions where neither of the proteins was overexpressed, Src immunoprecipitates were prepared from lysates of differentiating P19 cells and associated proteins were detected by phosphorylation with [$^{32}$P] ATP in vitro. Lysates from P19 cells were induced to differentiate with retinoic acid for three, five or seven days. The lysates were immunoprecipitated as described above with anti-Src or preimmune antibodies and incubated with [$\gamma^{32}$P]PATP to allow phosphorylation. Immunoprecipitation was carried out as described above, with the exception that after the four washes with TX-IXB, a further two washes were done with PAN buffer (100 mM NaCl, 10 mM PIPES (piperazine-N,N'-bis-2-ethanesulfonic acid) pH 7.0, 20 µg of aprotinin per ml) prior to incubation in UKB (10 mM PIPES (pH 7.0), 10 mM MnCl$_2$, 0.50 µM [$\gamma$-$^{32}$P]ATP (3,000 Ci/mmol)) for 15 minutes at 30° C. The reactions were stopped by elution of proteins described above. Labeled proteins were eluted and reimmunoprecipitated with either anti-Src, anti-mDab1 or preimmune antibodies. Samples analyzed by re-immunoprecipitation were lyophilized to remove the 2-mercaptoethanol, and then diluted 1:50 (from the original volume) into TX-IPB and mixed with antibodies overnight at 4° C. Proteins were visualized by autoradiography. Several labeled proteins including Src and proteins of approximately 60 and 80 kDa were observed.

To test whether mDab1 proteins were present, the radiolabeled proteins were eluted from the immunoprecipitates and reimmunoprecipitated with either preimmune serum, anti-Src antibody, or anti-mDab(B3). The p60 and p80 forms of mDab1 were recovered in the second immunoprecipitation of Src kinase reactions from differentiating but not control P19 cells. These results suggest that active Src and mDab1 p60 and p80 associate in differentiating P19 cells at the times when these mDab1 isoforms are found to be tyrosine phosphorylated and Src specific activity is elevated (Lynch et al., *Science* 234:873-876 (1986)).

f. Association of mDab1 with Tyrosine Phosphorylated Proteins

To examine whether the mDab1 PTB binds proteins that are tyrosine phosphorylated during neural development, a GST fusion protein containing the mDab1 PTB, a mutant mDab1 PTB in which Arg 56 was changed to Glu (mDab1 56E) or GST alone. was incubated with lysates from E13 mouse heads. Bound proteins were eluted, resolved and immunoblotted with anti-phosphotyrosine antibodies. The mDab1 PTB bound tyrosine phosphorylated proteins of 200, 120, 50-65 and 40 kDa. These proteins did not bind to GST alone.

To test whether the binding of proteins to the mDab1 PTB is phosphotyrosine dependent, binding experiments were done in the presence of the phosphotyrosine analog phenylphosphate. The assays was conducted as described above and phenylphosphate or phosphoserine were included in the binding buffer to investigate binding specificity. Proteins were eluted and analyzed as described above. Binding of the 120 and 40 kDa proteins were reduced significantly by phenylphosphate, and to a less extent by phosphoserine. However the binding of the 50-65 kDa proteins was not affected by either competitor.

To examine whether the mDab1 PTB may bind phosphoproteins directly, the mutant mDab1 56E, described above and containing an Arg to Glu substitution at amino acid 56, was tested. This residue is the equivalent of Arg 67 in the ShcA PTB, which contacts the phosphate moiety on the bound phosphopeptide (Zhou et al., ibid. (1995)). The mutant mDab1 56E bound the 120 kDa and 40 kDa embryonic head proteins less efficiently than the wild-type mDab1 PTB suggesting that the mDab1 PTB binds phosphorylated molecules in a similar manner to the ShcA PTB. The binding of the 55-60 kDa proteins to both the wild-type and the mutant mDab PTB, and in the presence of phosphoamino acid competitors, may suggest that the mDab PTB is also capable of protein-protein interactions independent of phosphorylation.

EXAMPLE VI

Disruption of the Mammalian Disabled1 (mdab1) Gene Disturbs Neuronal Layering in the Cerebral Cortex, Hippocampus and Cerebellum An mdab1-1 targeting vector for deletion of mDab1 was constructed by first inserting a blunted 0.9-kb BseRI-BglI fragment corresponding to intronic sequences 5' to the exon encoding residues 23 to 69 of the mdab1 gene in the PGKneolox2DTA vector (Soriano, *Devel.* 124:2691-2700 (1997); which is incorporated herein by reference). A 4-kb EcoRI-XbaI fragment from the mdab1 gene 3' to the same exon was Tinkered and was then ligated 3' into the SalI site between the PGKneo and PGK-DT sequences producing the targeting vector designated p80KO1. Plasmid p80KO1 was designed with the phosphoglycerate kinase (PGK) promoter driving neomycin phosphotransferase in place of 2 kb of genomic sequences that contained the first exon of the PI/PTB domain. Homologous sequences of 0.9 (5') and 4 kb (3') flank the PGKneo cassette. The targeting vector permitted nonhomologous integrants were counter-selected with the PGK-diphtheria toxin (DT) cassette.

The mDab1 gene was disrupted by homologous recombination with p80KO1 in embryonic stem cells. AK7 embryonic stem (ES) cells ($1\times10^7$) were electroporated with 20 µg linearized p80KO1. Cell culture and blastocyst injections were done as described by Soriano (ibid. (1991); which is incorporated by reference herein). Mice heterozygous for the altered allele (mdab1-1) were generated by standard blastocyst manipulation and mouse breeding. Genotyping of resulting mice was confirmed PCR genotyping using oligonucleotides P1 (5'-GTCAGGCTTCCTAAGTA-GAAAGGA-3') (SEQ ID NO:24), P2 (5'-TTCCAGGAGC-GAAATCACTCAACC-3') (SEQ ID NO:25), and P3 (5'-GGGAAAAGCGCCTCCCCTACCCGGT-3') (SEQ ID NO:26). Oligonucleotides P1 and P2 hybridize to genomic sequences outside the homologous regions and produce a 1.2 kb band by PCR amplification of the wild-type mdab1 allele. Oligonucleotides P1 and P3 (hybridizing to the 5' end of the PGK promoter) amplify a 0.95 kb fragment from the mdab1-1 mutant allele. In 200 births, homozygous mdab1-1 mutants were born with the expected frequency.

Western blot analysis of brain lysates from neonate F1 littermates probed with anti-mDab1(B3) polyclonal antibody demonstrated that the mDab1 p80 protein was absent in the homozygotes. mDab1 p80 is under-expressed in heterozygous animals and absent in the mdab1-1 homozygote. The 120 kDa immunoreactive protein which is present in wild-type and mutant animals is expressed early in development but not in adults and is either a spliced mdab1 gene product lacking the PI/PTB domain, or the product of a closely-related gene.

mdab1-1 homozygotes are outwardly normal until 10 days post partum (P10). By P15, it is apparent that mdab1-1 homozygotes are ataxic. They tremble, walk with a wide gait, drag their hind limbs, and frequently flip onto their backs. The mice generally die between P20 to P30. Similar phenotypes were observed with two independently-derived ES clones, and in 129Sv congenic or C57B16/129Sv hybrid genetic backgrounds.

Alterations in the mdab1-1 mutant brain were detected by histological examination of animals at P25. Animals were fixed by perfusion with 4% paraformaldehyde in phosphate buffered saline at 4° C. For anti-mDab1 immunofluorescence studies, the animals were fixed by perfusion with a solution of dimethyl sulfoxide and methanol (1:4).

Hematoxylin-eosin (H&E), Nissl, and Bielschowski staining were done following standard protocols. Coronal section of the neocortex were stained with Bielschowski stain, the hippocampus was stained with Hematoxylin-eosin and cerebellum was immunostained with anti-Calbindin antibody and counterstained with Nissl. Anti-CR 50, anti-BrdU (Becton Dickinson), and anti-calbindin immunohistochemistry was carried out as generally described (Ogawa et al., *Neuron* 14:899-912 (1995) and Chae et al., *Neuron* 18:29-42 (1997); which are incorporated by reference herein). A p80-specific antibody was generated by depleting mDab1 (B3) antibodies of reactivity to p120 by adsorption with lysates from mdab1-1 mutant brains. For birthdate analysis, BrdU was injected into pregnant mice (0.15 mg per g body weight) at indicated stage (Hoffarth et al., *J. Neurosci.* 15:4838-4850 (1995)). Immunofluorescence images were collected using a DELTAVISION microscope (Applied Precision Inc).

The brains of mdab1-1 mutant mice have multiple defects when studied at P25. The cerebral cortex of the mdab1-1 mutant stained with Bielschowski lacks the distinct cell layers of the wild-type mice. The cell-poor layer (marginal zone) under the pial (outer) surface is infiltrated by neurons in the mutant. Large pyramidal cells, normally deep in the cortex, can be detected in superficial layers. In addition, fibre bundles are detected coursing close to the pial surface, suggesting that afferent fibers are running obliquely instead of radially through the cortex (Goffinet, *Brain Res.* 319:261-296 (1984)). The hippocampus and the dentate gyrus in the mdab1-1 mice are also indistinct. Normally, large pyramidal neurons form a discrete layer marking the dentate gyrus and CA1 and CA3 regions of the hippocampus. In the mutant, the large pyramidal neurons are dispersed, although vestiges of the normal structures are visible.

The mutant cerebellum is small and has obviously altered structure. A normal P25 cerebellum has an outer cell-poor (molecular) layer, a single layer of Purkinje cells (PCs) with dendritic arbors extending into the molecular layer, a broad inner granule layer (IGL), and an underlying layer of white matter. This structure forms after birth. At birth, the wild-type cerebellum has PCs in a central mass and granule cells in an external granule layer (EGL). Starting at about PS, the PCs disperse to form a monolayer and the granule cells proliferate and migrate inward to form the IGL. The cerebellum of a mdab1-1 mutant at P25 was small and unfoliated, leaving the midbrain exposed, and resembles a prenatal wild-type cerebellum. The PCs appear to have matured normally, because they express both calbindin and zebrin II (Lannoo et al., *J. Comp. Neurol.* 310:215-233 (1991)), but they fail to disperse into a monolayer and their dendrites were randomly oriented. Perhaps as a result, normal PC-granule cell interactions were disrupted (Goffinet, *Anat. Embryol Berl.* 157: 205-216 (1979)), fewer granule cells mature, and although they migrate inward the majority remain superficial to the Purkinje cells. Where the EGL and PCs come into contact, the histology was more normal, suggesting that where PC-granule cell interaction was not seriously affected the granule cells develop more normally. Therefore the primary defect may be a failure of the PCs to disperse into a monolayer.

In the neocortex, the position and fate of a neuron is strongly correlated with the neuron's birthdate (McConnell et al., ibid. (1995)). Neurons born on successive days migrate past their predecessors, further outward from the neural tube (McConnell, *Curr. Opin. Neurobiol.* 2:23-27 (1992)). This has been shown by analyzing the brains of adults that were labeled in utero with thymidine analogues, such as 5-bromodeoxyuridine (BrdU). Cells undergoing their last S phase during the labeling period retain the label in their DNA, whereas cells that continue to cycle dilute the label over time. Most neurons that are marked early (embryonic day 11, E11) lie deep in the neocortex and differentiate as polymorphic cells, while most neurons marked on E16 end up in superficial layers and differentiate as small pyramidal cells. To test whether cortical neurons migrate correctly in mdab1-1 mutant mice, mice were treated in utero with BrdU and their brains analyzed at P25. Nuclei that were labeled with BrdU on E11 were found deep in the cortex of wild-type animals (layer VI) and superficial in the mdab1-1 mutants. Conversely neurons labeled on E16 were predominantly in the superficial cortex (layers II-III) of wild-type mice, but deep in the cortex of mdab1-1 mutant littermates. This showed that the final positions of cortical neurons are abnormal in mdab1-1 mutant mice. Because large pyramidal cells, normally located deep in the cortex, were found near the surface of the mutant cortex, the abnormal layering of the mutant cortex may result from altered migration of neurons without an alteration in fate.

These results indicated that mdab1-1 mutant mice were similar to the reeler mutant mice (Goffine, ibid. (1979); Caviness et al., *Brain Res.* 256:293-302 (1982); Hoffarth et al., ibid. (1995)). In both cases, the defects seen in the cortex are likely a consequence of altered neuronal migration indicating that mDab1 p80 and Reelin are involved in the same pathway that regulate neuronal migration. Reelin has been proposed to serve as a marker for the localization at which migrating cortical neurons come to rest (D'Arcangelo et al., *Nature* 374:719-723 (1995); Ogawa et al., ibid. (1995)). Reelin is expressed by pioneer Cajal-Retzius (CR) neurons, that are born early and occupy the outermost layer of the neocortex, immediately under the pia. p80 responds to the Reelin signal as demonstrated by an increase in mDab1 phosphorylation in response to Reelin protein.

In the mdab1-1 neocortex at E16 the CR cells are appropriately positioned and express Reelin, although other cells have already invaded the marginal zone. Therefore, mDab1 p80 is not required for Reelin production or CR cell migration. On the other hand, if p80 is needed to respond to the Reelin signal, it should be expressed in the migrating cortical neurons. p80 was localized in the E16 brain by immunofluorescence. p80 immunostaining was detected in essentially all neurons in the developing cortical plate and in the intermediate zone of the cerebral cortex of wild-type embryos. Only background levels of fluorescence were detected in the mutant cortex. This result shows that p80 is expressed by cortical neurons, including those that are migrating, and is consistent with a requirement for p80 in migrating neurons to respond to external signals such as Reelin.

In the E16 cerebellum, p80 was expressed in the region where the PCs were coalescing. p80 expression is also observed in mature PCs. p80 was not detected in the EGL, and it is unlikely that Bergmann glia express p80 because these cells have cytoplasmic projections across the EGL and no fluorescence was detected there. Because PCs in mdab1-1 mutants are malpositioned at P0 prior to the granule cell ingress, the primary defect in the mutant cerebellum may be due to defects in the PCs, and defects in granule cell number and position might be secondary. It has been shown previously that granule cells depend upon adjacent PCs for trophic support (Smeyne et al., *Mol. Cell. Neurosci.* 6:230-251 (1995)), and that granule cells make Reelin (Miyata et al., *J. Comp. Neurol.* 372:215-228 (1996)). Because Reelin expression was not altered in the mdab1-1 mutants and because mDab1 p80 was expressed by the affected cell types in the neocortex and cerebellum, it seems likely that mDab1 p80 acts cell-autonomously.

EXAMPLE VII

Comprehensive Screens for mDab1 PTB Domain Protein Ligands

To identify tyrosine-phosphorylated ligands for the mDab1 PTB domain a modified yeast two hybrid system was used to screen brain and hematopoietic cell cDNA libraries. The modified two hybrid system utilized a yeast strain that expressed the protein tyrosine kinase Src essentially as described by Keegan and Cooper (*Oncogene* 12:1537-1544 (1996)), Lioubin et al. (*Genes & Devel.* 10:1084-1095 (1996)) and PCT/US96/14754, each of which are incorporated by reference herein. The mDab1 PTB domain was expressed as a fusion protein with the LexA DNA binding domain, and brain and hematopoietic cell cDNA libraries were expressed as fusion proteins with a transcriptional activator domain. Interaction between mDab1 and the transcriptional activator fusion protein was assessed using two reporter genes that carry the LexA operator sequence, HIS3 and lacZ essentially as described above.

Transformation with the brain and hematopoietic libraries gave $3 \times 10^6$ and $0.3 \times 10^6$ yeast transformants, respectively. Of these, 72 clones were identified that expressed the HIS3 and lacZ genes in the presence of the LexA-mDab1 PTB fusion protein but not in the presence of a control LexA fusion protein. The 72 clones were re-tested for interaction with the LexA-mDab1 PTB fusion protein in the presence or absence of the PTK to determine if phosphorylation was required for the interaction. Surprisingly, in all instances lacZ expression was equal or slightly greater in the absence of kinase. Forty-eight clones identified from the brain library were sequenced. These clones fell into 6 classes, including the amyloid precursor protein (APP, represented 4 times) and LDL receptor related protein (LRP)/α-2 macroglobulin receptor (represented 2 times). Twenty-four clones analyzed from the hematopoietic library fell into 4 classes, including Ship (represented 18 times).

APP, LRP and Ship share very little sequence homology except for a short peptide sequence consisting of Asn Pro Xaa Tyr (NPXY). This sequence motif has been identified as a ligand for a number of other PTB domains.

The ability of the mDab1 PTB domain to interact directly with synthetic peptides based on the sequences identified in the two-hybrid screen was tested to identify the optimal sequence for mDab1 PTB domain binding. A GST-mDab1 PTB domain fusion protein was purified and radioactively-labeled by phosphorylation with protein kinase A and radioactive ATP. The purified, radioactive fusion protein was then incubated with a sheet of cellulose paper onto which different 15 to 17 residue synthetic peptides had been synthesized in a grid array (Niebuhr, et al., *EMBO J.* 16:5433-5444 (1997), incorporated herein by reference). Each sheet contained up to 100 different peptide sequences. After incubation, the sheet was washed and exposed to film, and bound PTB domain fusion protein was quantified. Auto-radiography of the filter after a binding reaction with a radioactively labeled GST-PTB domain fusion protein shows that differences in peptide sequence influences the amount of PTB bound. The mDab1 PTB domain was tested against peptides containing NPXY motifs from APP, the APP relatives APLP1 and APLP2, LRP, the LRP-related LDL receptor, Ship, and known ligands for the Shc and IRS-1 PTB domains, namely the EGF receptor, HER3 receptor, NGF receptor (TrkA), and insulin receptor. The mDab1 PTB domain was also tested against peptide motifs with phosphotyrosine in place of the tyrosine of the NPXY sequence (i.e. NPXpY peptides). The amount of radioactivity associated with each peptide was quantified with a PhosphorImager (Molecular Dynamics), and depicted as a percentage of that which associated with the APP peptide.

The mDab1 PTB domain bound to peptides containing the NPXY regions of APP, APLP1 and APLP2. In all three proteins, the sequence Gly Tyr Glu Asn Pro Thr Tyr Xaa Xaa Glu Xaa Xaa Xaa Xaa (SEQ ID NO:27) is conserved. Phosphorylation of the tyrosine of the NPXY motif in these peptides inhibited binding. LRP contains two NPXY motifs in its cytoplasmic tail. The more carboxy-terminal motif Asn Phe Thr Asn Pro Val Tyr (SEQ ID NO:28), and the corresponding sequence in the LDL receptor Asn Phe Asp Asn Pro Val Tyr (SEQ ID NO:29), were bound by the mDab1 PTB domain. However, the more N-terminal motif from the LRP bound poorly. Of the two NPXY containing peptides derived from p150 Ship sequence one bound Met Phe Glu Asn Pro Leu Tyr (SEQ ID NO:30) better than the other Glu Met Ile Asn Pro Asn Tyr (SEQ ID NO:31). The latter, when phosphorylated, is the binding site for the Shc PTB domain. Other known Shc PTB binding sites from the EGF receptor Asn Val Gly Asn Pro Glu Tyr (SEQ ID NO:32), and TrkA Ile Ile Glu Asn Pro Gln Tyr (SEQ ID NO:33), and the IRS-1 binding site on the insulin receptor Asn Ser Ser Asn Pro Glu Tyr (SEQ ID NO:34), failed to interact with the mDab1 PTB domain, whether phosphorylated or not. The peptides bound to the mDab1 PTB domain share a tyrosine or phenylalanine at position 5 residues N-terminal to the tyrosine of the NPXY sequence (i.e., the −5 position), suggesting that this residue may be important for binding.

To determine which residues in the APP sequence are involved in the interaction with the mDab1 PTB, an array of peptides based on the APP sequence with alanine substituted at each position in turn were synthesized. The ability of each peptide to bind to the PTB domain was compared to wild-type. The standard deviation of the procedure was shown to be +/−25%. The results demonstrated that most residues could be substituted with alanine with little or no effect on the amount of the mDab1 PTB domain that bound. However, substitution at Gly-6, Tyr-5, Asn-3 and Tyr-0 inhibited binding more than 90%, suggesting that the side chains of these residues are involved either in the interaction with the PTB domain or in the formation of a secondary structure that is required for the PTB domain interaction. Only the side chains of residues on the amino-terminal side of the NPXY motif appear to influence the strength of the interaction.

To determine the features of the APP peptide that were recognized by the mDab1 PTB domain, all nineteen amino acids, except cysteine, were substituted at several positions. In all cases the mDab1 PTB domain bound better to the wild-type APP sequence than to any altered sequence. Most substitutions of residues Gly-6, Tyr-5, Asn-3, Pro-2 and Tyr-0 inhibited PTB domain binding by greater than 80%. In place of Pro-2, isoleucine, lysine and arginine allowed 40% binding, suggesting some tolerance for substitutions at this position. Residue Tyr-5 could be replaced with tryptophan with minor reduction of amount of mDab1 PTB domain bound. Surprisingly, phenylalanine substitution of Tyr-5 resulted in a substantial reduction of binding. These results show that the wild-type APP sequence is optimal for binding to the mDab1 PTB domain, but does not exclude the possibility that a distinct sequence, containing multiple substitutions relative to the APP sequence, might bind equally or better. For example, the significant binding of the p150 Ship, LRP, and LDL receptor peptides implies that replacement of Tyr-5 with phenylalanine is permitted provided other changes are also made.

EXAMPLE VIII

Characterization of mDab1 PTB Domain-APP Binding

To test whether mDab1 would bind to the cytoplasmic tail of the APP protein, extracts of P19 cells were incubated with GST fusion proteins and subjected to immunoblot analysis as described above. Briefly, extracts of P19 cells, which express mDab1 p80, were incubated with a wild-type mDab1 PTB domain-GST fusion protein or an mDab56E-GST protein, containing the mutant mDab PTB domain described previously. Bound proteins were detected by SDS-PAGE followed by Western blotting. The immunoblot demonstrated that the APP protein clearly bound to the wild type, but not to the mDab1 56E PTB domain in vitro.

To test whether association occurs in vivo, 293T cells, which do not express mDab1 p80, were transfected with expression vectors for mDab555 p80 and for an epitope-tagged form of the cytoplasmic domain of APP (mT-APP). The p80 protein was immunoprecipitated with an anti-mDab1 antibody. Bound mT-APP was detected by SDS PAGE followed by Western blotting with antibodies to the epitope tag. The mT-APP protein was not immunoprecipitated from cells that were not expressing p80, but was precipitated from cells expressing mDab1 p80. These experiments suggest that the PTB domain of full-length mDab1 p80 can bind to the cytoplasmic domain of APP protein in cells. mDab1 p80 was not co-immunoprecipitated with endogenous, full-length APP from either P19 derived neurons or embryonic brain extracts. This may indicate either that endogenous p80 and APP are not in proximity in intact cells, or that the antibodies to p80 and APP are inadequate to detect the association.

The affinity of the interaction between the mDab1 PTB domain and the APP synthetic peptide was determined by fluorescence depolarization (Li et al., *Proc. Natl. Acad. Sci. USA*, 74:7204-7209 (1997) incorporated herein by reference). When a fluorescently-labeled peptide is excited with polarized light, it emits fluorescence that is partially depolarized. The extent of depolarization depends on the rotational diffusion of the fluor. When bound to a large protein, such as a PTB domain, the rate of tumbling is reduced, and the emitted light retains greater polarization. The amount of residual fluorescence polarization is thus directly proportional to the percentage of fluorescent peptide that is bound to the protein. When trace amounts (approximately 1 nM) of fluorescein-labeled APP peptide was incubated with increasing amounts of the GST-mDab1 PTB domain, fluorescence polarization increased, allowing a calculation of the percent of the fluorescent peptide bound. A Gaussian relationship was observed between the fraction of APP bound and the log of the concentration of GST-PTB in the solution. The concentration of mDab1 PTB required for half maximal binding, i.e. the dissociation constant was found to be 0.55 µM.

The relative affinity of the phosphorylated peptide was determined by competition assay. Non fluorescent peptide competitors were added to a solution where 75% to the fluorescein-labeled APP peptide was bound by the GST-PTB domain. Addition of increasing amounts of unphosphorylated APP peptide resulted in a decrease in the fraction of fluorescein-labeled APP peptide bound, but addition of much higher concentrations of the phosphorylated APP peptide were required to produce a modest decrease in the fraction of fluorescein-labeled APP peptide bound. Phosphatase treatment of the phosphopeptide restored its ability to compete for fluorescein-labeled APP peptide binding. The reactions contained 1.1 µM PTB domain, tracer fluorescent peptide, and different concentrations of non-fluorescent peptide or phosphopeptide. Five hundred micromolar phosphopeptide was found to be as effective as 2 µM peptide in reducing binding of the fluorescent tracer to the PTB domain. The phosphopeptide became an effective competitor if incubated with a phosphatase, however, showing that there was not an intrinsic defect in the phosphopeptide or a contaminant in the binding reaction. Thus, the binding to non-phosphorylated peptide is approximately 0.5 µM, and phosphorylation reduces the affinity 250-fold.

EXAMPLE IX

Determination of mDab1 Phosphotyrosine Binding Domain Interaction with Phosphoinositide Previously PTB domain three-dimensional fold has been shown to resemble a pleckstrin-homology (PH) domain. Zhou et al., ibid. (1995) tested whether the Shc PTB domain share with the PH domains an affinity for phosphoinositides. Binding was assayed by mixing the soluble Shc OH domain with large unilamellar vesicles (LUVs) containing neutral phospholipids and various anionic phospholipids, followed by centrifugation to separate the LUV-associated from the free Shc PTB domain. A similar assay has been used to test whether the mDab1 PTB domain also bound phospholipids.

GST fusion proteins containing the Shc or mDab1 PTB domain were compared for their ability to bind LUVs that contained phosphotidylisositol 4,5 P2 (PtdIns4,5P2), phosphatidylserine (PtdSer) and phosphatidylethanolamine (PtdEth). Methods for the production of LUVs and assays for binding to Shc phosphotyrosine-binding domains can found in Ravichandran, et al., *Mol. Cell. Biol.* 17:5540-5549 (1997) which is incorporated herein by reference. After the fusion proteins and a GST control were incubated with the LUVs the reactions were centrifuged and the presence of the fusion proteins were detected by SDS PAGE and Western blotting with antibodies to GST as described above. GST-Shc PTB and GST-mDab1 PTB fusion proteins were found in the high speed pellet fraction in the presence of but not in the absence of LUVs. While the GST fusion protein control was found in the high speed supernatant in the presence of absence of the LUVs. These results indicate that mDab1, like Shc PTB, binds to LUVs containing mixed phospholipids.

The specificity of mDab1 PTB binding to phospholipids was also determined. For these studies LUVs were prepared containing equal quantities of PtdSer, phosphatidylcholine (PtdCho) and Ptd Eth, and 0 or 5% by weight of PtdIns4P, PtdIns4,5P2, or PdtIns3,4,5P3. This corresponded to approximately 7.5 µM phosphoinositide in the outer leaflet of the lipid bilayer. Detection of binding to the LUVs was determined as described above.

GST-mDab1 PTB was found to bind to LUVs containing various phosphoinositides, but was unable to bind to LUVs lacking phosphoinositide. The efficiency of binding to the various phosphoinositides was found to vary with PdtIns3, 4,5P3 being less than that to PtdIns4P or PtdIns4,5P2. Binding of mDab1 PTB to nonphosphorylated PtdIns was also found to be inefficient.

mDab1 PTB binding to LUVs containing phosphoinositides in the presence of various phosphorylated isomers of inositol was also examined to determine whether the binding of mDab1 PTB to phosphoinositides was specific or was the result of a strong affinity for strongly anionic phospholipids. GST-mDab1 PTB binding to LUVs containing PtdIns4,5P2 was tested in the presence of 100 µM D-Inst1, 4,5P3, L-Ins1,4,5P3 and other inositol phosphates. Binding was competed with D-Ins1,4,5P3, but not by L-Ins1, 4,5P3. When tested at 30 µM, weak competition was detected with D-Ins1,4,5P3 and not other inositol phosphates. The pattern of competition obtained suggested that the mDab1 PTB domain specifically recognized the phosphorylated isositol headgroup present on PtdIns4,5P2. The stereospecificity implies that the phosphates on the phosphoinositide bind to specific sites on the PTB domain, and that the PTB domain does not bind to all highly-phosphorylated compounds. However, the concentration of inhibitor needed to reduce binding was high, suggesting that binding to the phosphoinositide may also be of low affinity.

The GST fusion proteins were also tested to determine if possible dimerization of the fusion protein altered to binding specificity of the PTB to multimeric ligands, such as an LUV containing many molecules of PtdIns4,5P2. The effects of dimerization were tested by cleaving the GST-mDab1 fusion protein with thrombin prior to incubating the PTB with LUV containing PtdIns4,5P2. Released GST was found not to bind to the LUVs, but cleaved mDab1 and uncleaved fusion protein were found to bind to the LUVs with similar efficiency. These results suggested that GST-mediated dimerization would not artificially raise the apparent affinity determined for the mDab1 PTB when tested as a GST fusion protein.

Although the foregoing invention has been described in some detail by way of illustration and example for purposes of clarity of understanding, it will be obvious that certain changes and modifications may be practiced within the scope of the invention. All publications and patents mentioned in this specification are herein incorporated by reference into the specification to the same extent as if each individual publication or patent was specifically and individually indicated to be incorporated herein by reference.

What is claimed is:

1. An isolated and purified polynucleotide that encodes the murine Dab 1 (Disabled protein 1) as depicted in SEQ ID NO: 3, or the complement thereof wherein said polynucleotide is not genomic DNA.

2. The polynucleotide of claim 1, which is cDNA sequence.

3. An isolated probe comprising an oligonucleotide of at least 25 nucleotides obtained from the nucleotide sequence as depicted in SEQ ID NO: 2 and which specifically hybridizes at 65-68° C. in an aqueous solution containing 4-6X SSC with a polynucleotide sequence which encodes a murine Disabled protein 1 as depicted in SEQ ID NO: 3, or the complement thereof.

4. The probe of claim 3, which is at least 50 nucleotides in length.

5. The probe of claim 3, which further comprises a detectable signal.

6. A DNA construct comprising the following operably linked elements:
   a transcriptional promoter;
   a DNA sequence encoding the murine Disabled protein 1 as depicted in SEQ ID NO: 3, or the complement thereof; and
   a transcriptional terminator.

7. The DNA construct of claim 6, wherein the DNA sequence encoding a murine Disabled protein 1 is the oligonucleotide sequence depicted in SEQ ID NO:2.

8. A DNA construct comprising the following operably linked elements:
   a transcriptional promoter;
   a DNA sequence encoding a fragment of the murine Disabled protein 1 consisting of residues 107 to 243 of SEQ ID NO: 3; and
   a transcription terminator.

9. A cultured host cell transformed or transfected with a DNA construct which comprises the following operably linked elements:
   a transcriptional promoter operable in the host cell;
   a DNA sequence encoding the murine Disabled protein 1 as depicted in SEQ. ID. NO: 3, or the complement thereof, and
   a transcriptional terminator operable in the host cell.

10. The host cell of claim 9, wherein the host cell is a prokaryotic or eukaryotic cell.

11. The host cell of claim 10, wherein the prokaryotic cell is a bacterial cell.

12. The host cell of claim 10, wherein the eukaryotic cell is a yeast cell or a mammalian cell.

* * * * *